United States Patent
Singer et al.

(10) Patent No.: US 10,119,140 B2
(45) Date of Patent: Nov. 6, 2018

(54) METHODS FOR ENHANCING OR DECREASING THE LEVELS OF MIR124 AND MIR29 IN SUBJECTS WITH MUSCULAR DYSTROPHY

(71) Applicant: Board of Regents of the Nevada System of Higher Education, on Behalf of The University of Nevada, Reno, NV (US)

(72) Inventors: Cherie A. Singer, Sparks, NV (US); Ryan Wuebbles, Reno, NV (US); Dean Burkin, Reno, NV (US)

(73) Assignee: BOARD OF REGENTS OF THE NEVADA SYSTEM OF HIGHER EDUCATION ON BEHALF OF THE UNIVERSITY OF NEVADA, RENO, Reno, NV (US)

( * ) Notice: Subject to any disclaimer, the term of this patent is extended or adjusted under 35 U.S.C. 154(b) by 0 days.

(21) Appl. No.: 15/305,058

(22) PCT Filed: Apr. 17, 2015

(86) PCT No.: PCT/US2015/026475
§ 371 (c)(1),
(2) Date: Oct. 18, 2016

(87) PCT Pub. No.: WO2015/161255
PCT Pub. Date: Oct. 22, 2015

(65) Prior Publication Data
US 2017/0088837 A1 Mar. 30, 2017

Related U.S. Application Data

(60) Provisional application No. 61/981,631, filed on Apr. 18, 2014.

(51) Int. Cl.
| | | |
|---|---|---|
| *C12N 15/113* | (2010.01) | |
| *C12N 15/11* | (2006.01) | |
| *C12Q 1/6883* | (2018.01) | |
| *A61K 31/713* | (2006.01) | |
| *A61K 45/06* | (2006.01) | |

(52) U.S. Cl.
CPC .......... *C12N 15/113* (2013.01); *A61K 31/713* (2013.01); *A61K 45/06* (2013.01); *C12N 15/111* (2013.01); *C12Q 1/6883* (2013.01); *C12N 2310/113* (2013.01); *C12N 2310/141* (2013.01); *C12N 2320/30* (2013.01); *C12Q 2600/158* (2013.01); *C12Q 2600/178* (2013.01)

(58) Field of Classification Search
CPC .................. C12N 15/113; C12N 2310/141
See application file for complete search history.

(56) References Cited

FOREIGN PATENT DOCUMENTS

WO    WO 2013/090457    6/2013

OTHER PUBLICATIONS

Qadir et al. Journal of Cellular Biochemistry 115:1572-1581 (Year: 2014).*
Greco et al., "Common micro-RNA signature in skeletal muscle damage and regeneration induced by Duchenne muscular dystrophy and acute ischemia," *FASEB J.*, vol. 23, pp. 3335-3346, 2009.
Marrone et al., "Dg-Dys-Syn1 signaling in *Drosophila* regulates the microRNA profile," *BMC Cell Biology*, 13:26, 2012 (18 pages).
Singer et al., "Integrin α7 expression in airway smooth muscle cells is inhibited by Mir-124a and Mir-291," *American Journal of Respiratory and Critical Care Medicine*, Abstract 2105, published online May 1, 2014 (3 pages).

* cited by examiner

*Primary Examiner* — Brian A Whiteman
(74) *Attorney, Agent, or Firm* — Schwabe, Williamson & Wyatt

(57) ABSTRACT

Disclosed herein are methods of treating and diagnosing muscular dystrophy. In some examples, the methods include treating muscular dystrophy by administering to the subject a therapeutically effective amount of an agent that alters the expression of at least one miR gene product, such as miRNA-124 and/or miRNA-29 thereby treating muscular dystrophy. In one particular example, the method of treatment includes administering an agent that decreases the expression or activity of miRNA-124. In another embodiment, the method of treatment includes administering a composition that includes one or more agents to decrease the expression and/or activity of miRNA-124 and one or more agents to alter the activity of miRNA-29 (increase or decrease). Also disclosed are methods of enhancing muscle regeneration, repair, or maintenance in a subject and methods of enhancing α7β1 integrin expression. Methods of prospectively preventing or reducing muscle injury or damage in a subject are also disclosed.

13 Claims, 7 Drawing Sheets

FIG. 1B miRNA-124a Levels miRNA-124a/U6 levels in Tricep muscles from 3-month old wild-type and *mdx* mice FIG. 1C miRNA-29a Levels miRNA-29a/U6 levels in Tricep muscles from 3-month old wild-type and *mdx* mice miRNA-124a/U6 levels in Tricep muscles from 12-month old wild-type and *mdx* mice miRNA-29a/U6 levels in Tricep muscles from 12-month old wild-type and *mdx* mice miRNA-124a/U6 levels in Human DMD myoblasts and myotubes miRNA-29a/U6 levels in Human DMD myoblasts and myotubes

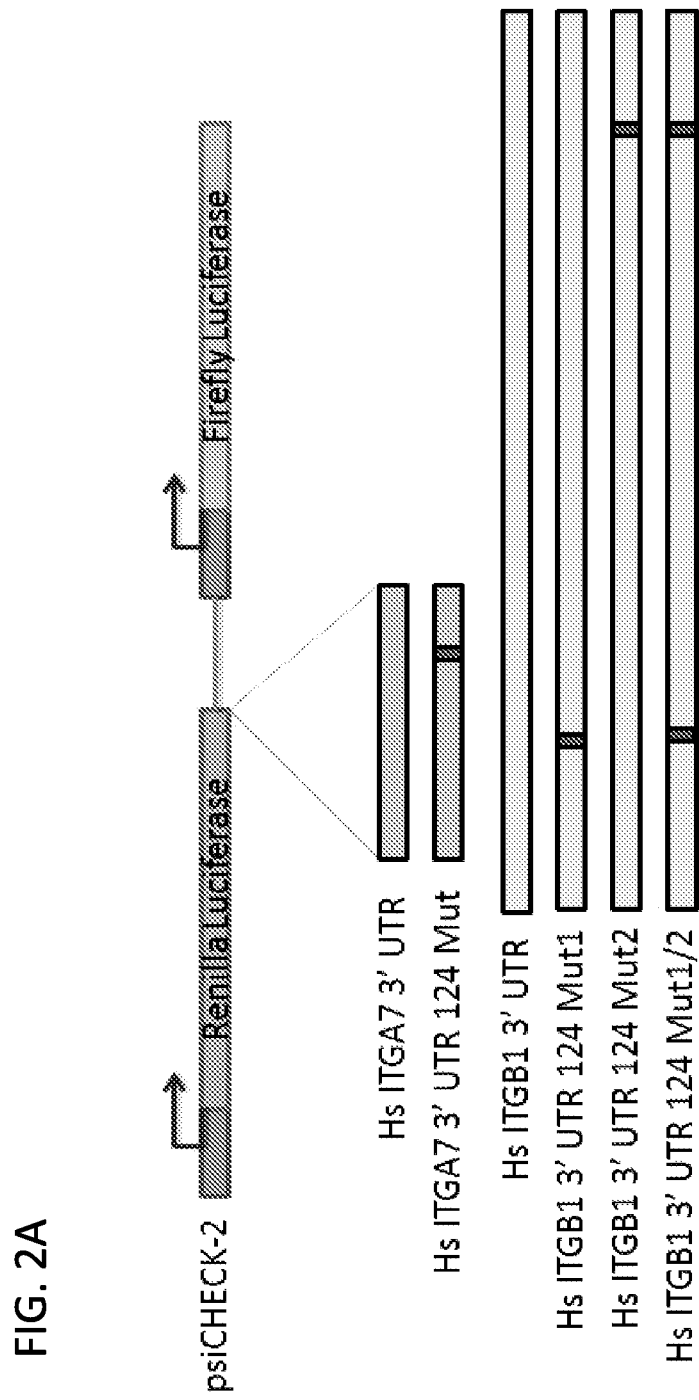

METHODS FOR ENHANCING OR DECREASING THE LEVELS OF MIR124 AND MIR29 IN SUBJECTS WITH MUSCULAR DYSTROPHY

CROSS REFERENCE TO RELATED APPLICATION

This application is the § 371 U.S. National Stage of International Application No. PCT/US2015/026475, filed Apr. 17, 2015, which was published in English under PCT Article 21(2), which in turn claims the benefit of U.S. Provisional Application No. 61/981,631, filed Apr. 18, 2014, which is incorporated herein by reference in its entirety.

ACKNOWLEDGMENT OF GOVERNMENT SUPPORT

This invention was made with government support under Grant Number R01 AR053697 awarded by the National Institutes of Health. The government has certain rights in the invention.

FIELD

This disclosure concerns microRNAs (miRNAs), such as miR-124 and miR-29, that are expressed in subjects with muscular dystrophy, and use of the disclosed miRNAs for the diagnosis and treatment of muscular dystrophy, such as Duchenne muscular dystrophy (DMD), Fukuyama congenital muscular dystrophy (FCMD) or merosin deficient congenital muscular dystrophy type (MDC)1A or 1D.

BACKGROUND

Mutations in the α7 integrin gene are responsible for congenital myopathy in man. The α7β1 integrin is also a major modifier of muscle disease progression in various genetic muscle diseases including various types of muscular dystrophy, such as Duchenne muscular dystrophy (DMD), Fukuyama congenital muscular dystrophy (FCMD) and merosin deficient congenital muscular dystrophy type 1A (MDC1A). However, transcriptional regulation of the α7 integrin gene, including such role in muscular dystrophy (e.g., DMD, FCMD and/or MDC1A), remains poorly understood.

Duchenne muscular dystrophy (DMD) is an X-chromosome-linked disease and the most common form of muscular dystrophy. DMD affects 1 in 3500 live male births with patients suffering from chronic muscle degeneration and weakness. Clinical symptoms are first detected between the ages of 2 and 5 years and, by the time the patient is in their teens, the ability for independent ambulation is lost. Death typically occurs in the patient before they are 30 years old due to cardiopulmonary failure.

Fukuyama congenital muscular dystrophy (FCMD) and MDC1A are congenital muscular dystrophies that are heritable neuromuscular disorders. MDC1A is characterized by muscle weakness at birth or in infancy. Affected infants will present with poor muscle tone and few movements. The quality of life and life span of the child is affected through progressive muscle wasting, respiratory compromise, and spinal rigidity. MDC1A is the most common and severe form of congenital muscular dystrophy, accounting for 30-40% of all congenital muscular dystrophy (CMD) diagnosed cases. MDC1A is characterized by congenital hypotonia, distinct joint contractures, and a lack of independent ambulation. Feeding tube placement and positive pressure ventilation is often required for the respiratory problems that occur. Patients afflicted with MDC1A often die before they reach the age of ten years. FCMD is caused by mutations in the fukutin gene, located at human chromosome 9q31. The disease is inherited in an autosomal recessive manner. FCMD is a type of Limb-Girdle muscular dystrophy. Currently there is no cure for DMD, FCMD or MDC1A.

SUMMARY

The muscular dystrophies are a group of diverse, heritable neuromuscular disorders which represent a group of devastating neuromuscular diseases characterized by primary or secondary skeletal muscle involvement. Currently, there are no cures for such diseases.

Disclosed herein are methods of treating and diagnosing muscular dystrophy, such as DMD, FCMD or MDC1A. In some embodiments, the methods include treating muscular dystrophy by administering to the subject a therapeutically effective amount of an agent that alters the expression of at least one miR gene product, such as miRNA-124 and/or miRNA-29 thereby treating muscular dystrophy, such as DMD, FCMD or MDC1A. In one particular embodiment, the method of treatment includes administering an agent that decreases the expression or activity of miRNA-124. In another embodiment, the method of treatment includes administering a composition that includes one or more agents to decrease the expression and/or activity of miRNA-124 and one or more agents to alter the activity of miRNA-29, such as increase or decrease the activity of miRNA-29.

Also provided are methods of diagnosing which include detecting expression of at least one miR gene product, such as miRNA-124 and/or miRNA-29, in a sample obtained from the subject; comparing expression of the at least one of the miR gene product in the sample obtained from the subject to a control (such as a reference standard), wherein altered expression of the at least one miR gene product, such as an increase in miRNA-124 and/or a decrease or increase in miRNA-29 expression, in the sample obtained from the subject compared to the control indicates that the subject has muscular dystrophy such as DMD, FCMD or MDC1A.

Further provided are methods of determining the effectiveness of an agent for the treatment of muscular dystrophy, such as DMD, FCMD or MDC1A, in a subject. In some examples, this method includes detecting expression of at least one miR gene product in a sample, such as miRNA-124 and/or miRNA-29, from the subject following treatment with the agent; and comparing expression of the at least one miR gene product following treatment to a reference value, wherein an alteration in the expression of the at least one miR gene product following treatment indicates that the agent is effective for the treatment of muscular dystrophy, such as DMD, FCMD or MDC1A, in the subject. In some examples, the reference value represents an expression value of the at least one miR gene product in a sample from the subject prior to treatment with the agent. In some examples, the at least one miR gene product is miRNA-124 and/or miRNA-29 and an at least two-fold decrease in the expression of miRNA-124 and/or an two-fold increase in miRNA-29 following treatment indicates that the agent is effective for the treatment of muscular dystrophy in the subject.

The foregoing and other features and advantages of the disclosure will become more apparent from the following detailed description, which proceeds with reference to the accompanying figures.

BRIEF DESCRIPTION OF THE DRAWINGS

FIGS. 1A-1G illustrates that miRNA-124 and miRNA-29 are significantly altered in mdx muscle relative to wild-type. FIG. 1A is a schematic illustrating evolutionarily conserved miRNA-124a and mmiRNA-29 sites located with the human 3' UTRs of ITGA7, ITGB1 and LAMA2 transcripts as predicted using TargetScan. Quantitative real-time PCR for the levels of miRNA-124a and miRNA-29 are shown in FIGS. 1B, 1D and 1F and FIGS. 1C, 1E and 1G, respectively. Total RNA was purified from 3-month old wild-type and mdx triceps (See FIGS. 1B and 1C), 12-month old wild-type and mdx triceps (FIGS. 1D and 1E) or from cultured human DMD primary myoblasts and 10-day differentiated myotubes (FIGS. 1F and 1G). miR-124 and miR-29 levels were analyzed by Taqman primers and normalized to U6 snRNA.

Significance was calculated with Graphpad Prism software using an unpaired t-test with $*p<0.05$, $<0.01$ and $*p<0.001$.

Figure 2B:
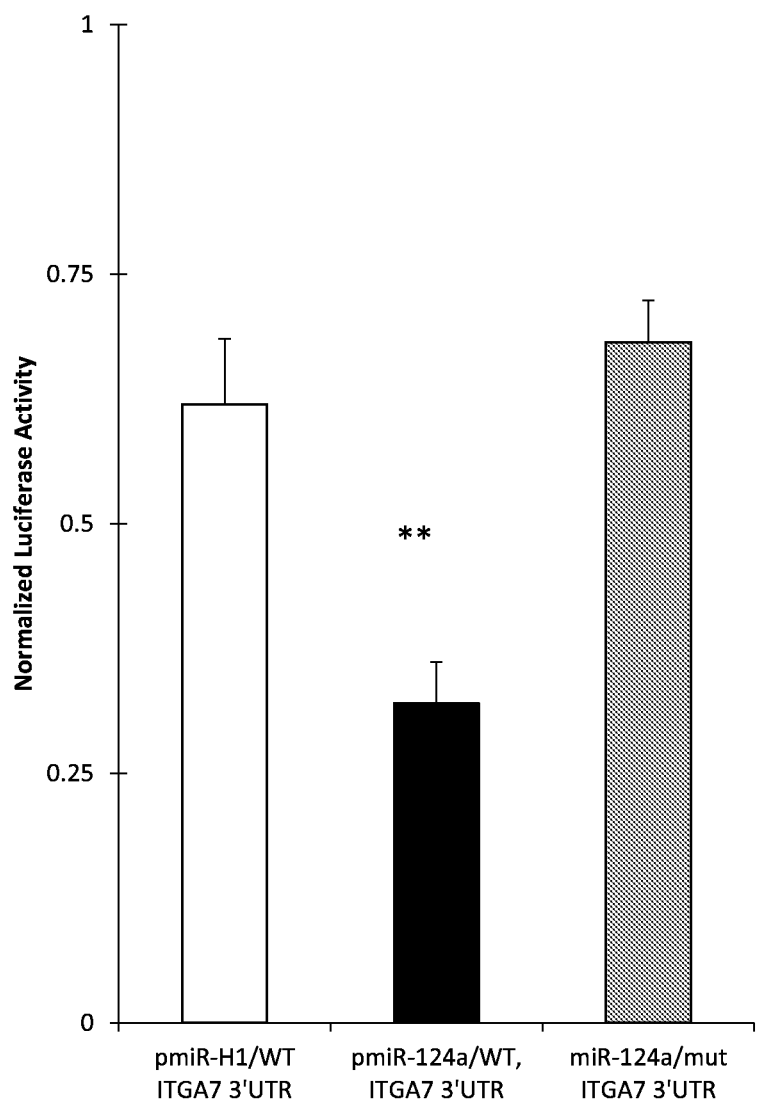
Figure 2C:
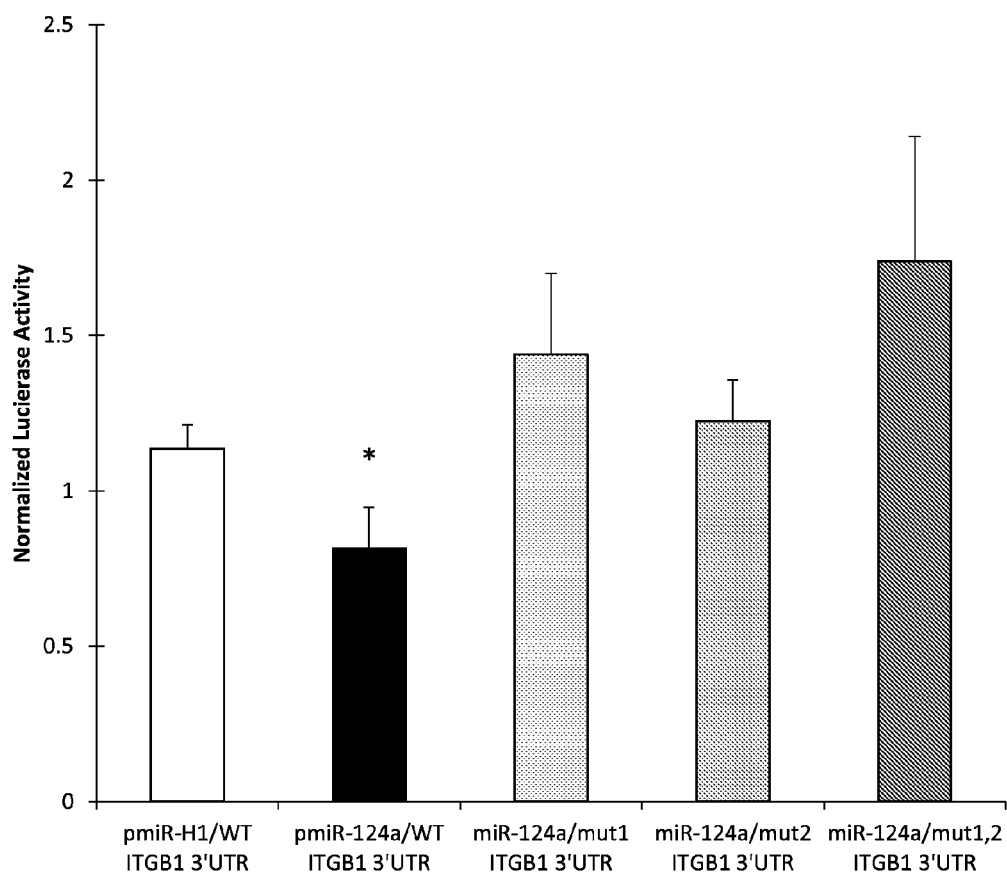

FIGS. 2A-2C illustrates that miR-124 binds to the wild-type 3' untranslated region (UTR) of the α7 integrin (ITGA7) and β1 integrin (ITGB1) genes relative to the vector control and compared to seed-sequence binding mutants. FIG. 2A is a schematic depicting the psiCHECK-2 vector and the location of the Human ITGA7 and ITGB1 3' UTRs as well as the sites of the miR-124 seed sequence mutations. FIGS. 2B and 2C are bar graphs illustrating the results of dual-luciferase miRNA binding assays for miR-124a. HEK-293 cells overexpressing a lentivirus encoding the control vector pmiR-H1 or precursor miRNA specific for pmiR-124a were transfected with the 3'UTR of (A) ITGA7 or (B) ITGB1 or the mutants described above for 48 h. Luciferase activity was measured in cell lysates using the Dual-Luciferase Assay System (Promega, Madison, Wis.) on a luminometer. Renilla activity was normalized to firefly luciferase activity and the results presented as means+SEM from 5-6 replicates.* $P<0.05$ from cells transfected with ITGB1 mutants; ** $P<0.01$ from cells transfected with WT or ITGA1 mutants.

Figure 3:
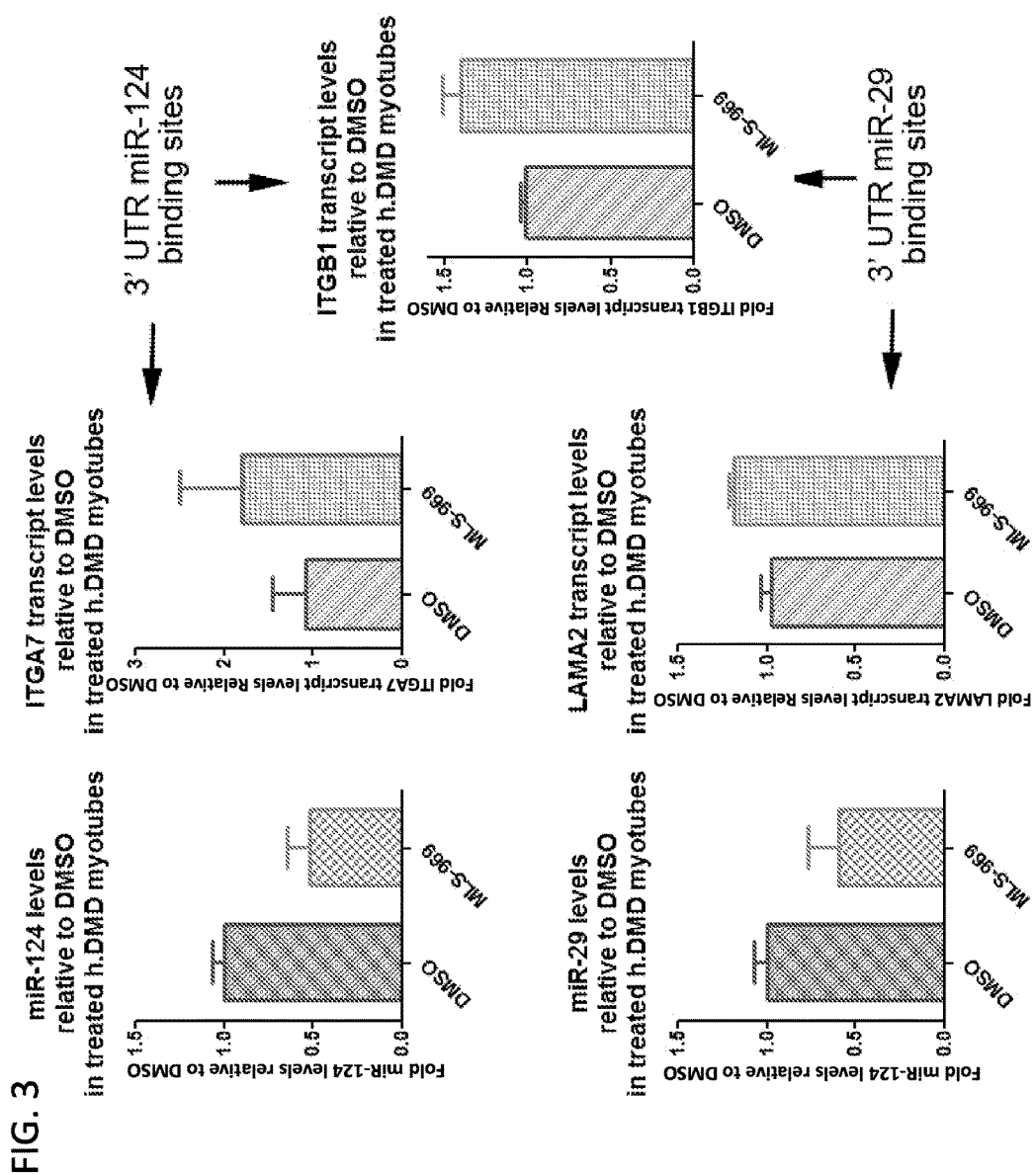

FIG. 3 illustrates small molecules known to increase α7 integrin levels also decrease miR-124 and miR-29 levels. In Human DMD myotubes, the levels of miR-124 and miR-29 are downregulated MLS000532969 (MLS-969) treatment. A corresponding increase in ITGA7, ITGB1, and LAMA2 transcripts is observed with MLS-969 treatment. MLS-969 is a novel α7 Integrin enhancing compound.

Figure 4:
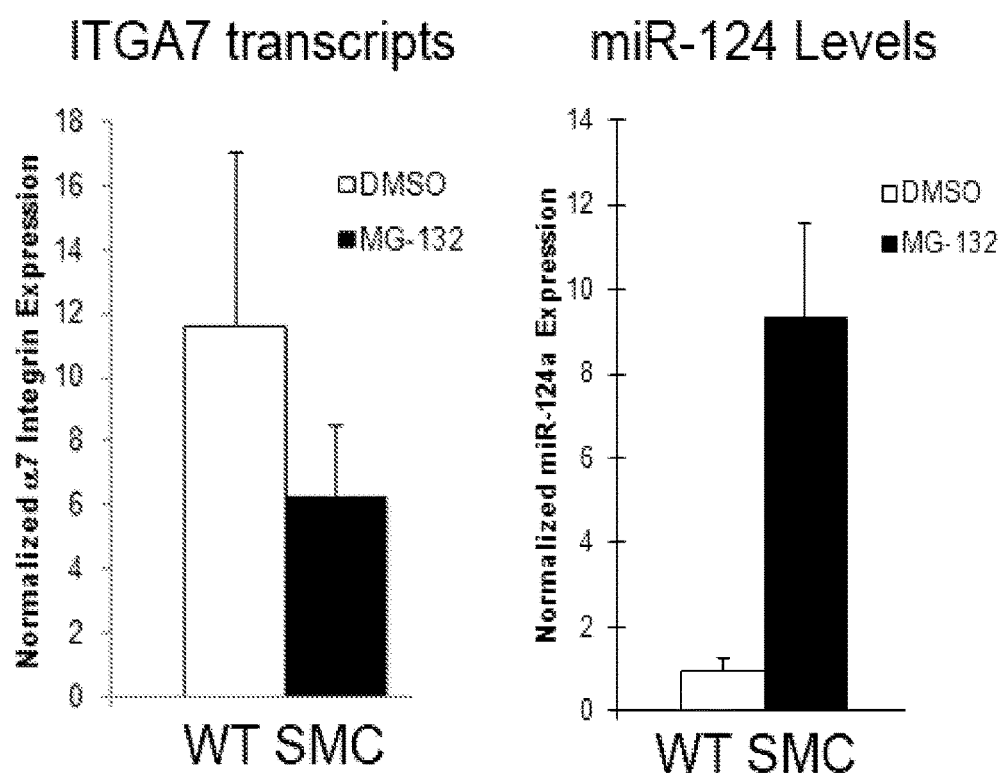

FIG. 4 illustrates known inhibitors of integrin α7 Integrin expression regulate miR-124a expression wild-type smooth muscle cells (WT SMC). WT SMC were plated at a density of 35,000 cells/6 well and grown in M199+FBS and growth factors prior to differentiation for 5 days in serum-free DMEM/F12. Cultures were then treated with 10 mM MG-132 for 48 hours. Total RNA was isolated to measure miRNA or mRNA, n=3-6+SEM*p<0.05.

DETAILED DESCRIPTION

I. Terms

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art.

All publications, patent applications, patents, and other references mentioned herein are incorporated by reference in their entirety. All sequences provided in the disclosed Genbank Accession numbers and miRBase Accession numbers are incorporated herein by reference as available on Apr. 18, 2014. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administration: To provide or give a subject one or more agents, such as an agent that increases α7β1 expression and/or treats one or more symptoms associated with muscular dystrophy, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Agent: Any protein, nucleic acid molecule (including chemically modified nucleic acids), compound, antibody, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including treating a subject with a muscular dystrophy).

In some examples, an agent can act directly or indirectly to alter the expression and/or activity of a miRNA-124 or miRNA-29. For example, a "therapeutic agent" is a chemical compound, small molecule, or other composition, such as an antisense compound, antibody, protease inhibitor, hormone, chemokine or cytokine, capable of inducing a desired therapeutic or prophylactic effect when properly administered to a subject. In some examples, the therapeutic agent includes an isolated miRNA gene product that is down-regulated in patients with muscular dystrophy or an inhibitor of an miRNA that is up-regulated in patients with muscular dystrophy. In a particular example, a therapeutic agent significantly decreases the activity or expression of miRNA-124 or miRNA-124 gene product (which are muscular dystrophy associated molecules) thereby treating one or more signs or symptoms associated with muscular dystrophy. An example of a therapeutic agent is one that can decrease expression and/or activity of miRNA-124 or gene product, for example as measured by a clinical response (such as a decrease in one or more signs or symptoms associated with the muscular dystrophy, an improvement in muscular health, regeneration, repair or maintenance of a muscle cell or tissue). "Improving muscular health" refers to an improvement in muscular health compared with a pre-existing state or compared with a state which would occur in the absence of treatment. For example, improving muscular health may include enhancing muscle regeneration, maintenance, or repair. Improving muscular health may also include prospectively treating a subject to prevent or reduce muscular damage or injury. "Regeneration" refers to the repair of cells or tissue, such as muscle cells or tissue (or organs) which includes muscle cells, following injury or damage to at least partially restore the muscle or tissue to a condition similar to which the cells or tissue existed before the injury or damage occurred. Regeneration also refers to facilitating repair of cells or tissue in a subject having a disease affecting such cells or tissue to eliminate or ameliorate the effects of the disease. In more specific examples, regeneration places the cells or tissue in the same condition or an improved physiological condition as before the injury or damage occurred or the condition which would exist in the absence of disease. "Maintenance" of cells or tissue, such as muscle cells or tissue (or organs) which includes muscle cells, refers to maintaining the cells or tissue in at least substantially the same physiological condition, such as maintaining such condition even in the presence of stimulus which would normally cause damage, injury, or disease. "Repair" of cells or tissue, such as muscle cells or tissue (or organs) which includes muscle cells, refers to the physiological process of healing damage to the cells or tissue following damage or other trauma.

A "pharmaceutical agent" is a chemical compound or composition capable of inducing a desired therapeutic or prophylactic effect when administered to a subject, alone or in combination with another therapeutic agent(s) or pharmaceutically acceptable carriers. In a particular example, a pharmaceutical agent significantly decreases the expression and/or activity of miRNA-124 and/or increases the expression of miRNA-29, thereby treating a condition or disease associated with altered expression/activity of miRNA-124 and/or miRNA-29, such as muscular dystrophy.

Alteration in expression: An alteration in expression of a miR gene product refers to a change or difference, such as an increase or decrease, in the level of the miR gene product that is detectable in a biological sample relative to a control. An "alteration" in expression includes an increase in expression (up-regulation) or a decrease in expression (down-regulation). In some examples, an alteration in expression includes a change or difference, such as an increase or decrease, in the conversion of the information encoded in a microRNA gene into microRNA gene product. In some examples, the difference is relative to a control or reference value, such as an amount of microRNA expression in a sample from a healthy control subject.

Antisense compound: An oligomeric compound that is at least partially complementary to the region of a target nucleic acid molecule (such as a miRNA gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In some examples, the target nucleic acid molecule is a miRNA gene product (such as those indicated as miRNAs upregulated in a subject with muscular dystrophy, such as miRNA-124).

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA or ribozyme.

In some examples, an antisense compound is an "antisense oligonucleotide." An antisense oligonucleotide is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Array: An arrangement of molecules, such as biological macromolecules (such nucleic acid molecules), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least 2, at least 5, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-1000 addressable locations, such as 10-100 addressable locations. In particular examples, an array consists essentially of probes or primers (such as those that permit amplification) specific for the miR gene products.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biological activity: The beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, the agent significantly decreases the biological activity of miRNA-124 and/or increases the expression of miRNA-29 which reduces one or more signs or symptoms associated with the muscular dystrophy, muscle aging and other muscle related disorders.

Biological sample (or sample): A biological specimen containing genomic DNA, RNA (including mRNA and microRNA), protein, or combinations thereof, obtained from a subject. Examples include, but are not limited to, saliva, peripheral blood, serum, urine, tissue biopsy, surgical specimen, and autopsy material. In one example, a sample includes a biopsy of an adrenal cortex, such as from a healthy control subject. In other embodiments, the biological sample is blood, or a component thereof, such as plasma or serum.

Contacting: Placement in direct physical association, including both a solid and liquid form. Contacting an agent with a cell can occur in vitro by adding the agent to isolated cells or in vivo by administering the agent to a subject.

Control: A sample or standard used for comparison with a test sample, such as a biological sample obtained from a patient (or plurality of patients) without a particular disease or condition, such as a muscular dystrophy. In some embodiments, the control is a sample obtained from a healthy patient (or plurality of patients) (also referred to herein as a "normal" control), such as a normal biological sample. In some embodiments, the control is a historical control or standard value (e.g., a previously tested control sample or group of samples that represent baseline or normal values (e.g., expression values), such as baseline or normal values of a particular miRNA such as miRNA-124 or miRNA-29 gene, gene product in a subject without a muscular dystrophy). In some examples, the control is a standard value representing the average value (or average range of values) obtained from a plurality of patient samples (such as an average value or range of values of the gene or gene products, such as miRNA-124 or miRNA-29 or gene products thereof, in the subjects without a muscular dystrophy).

Decrease: To reduce the quality, amount, or strength of something. In one example, a therapy decreases one or more symptoms associated with the muscular dystrophy, for example as compared to the response in the absence of the therapy.

In some examples, when used in reference to the expression of nucleic acid molecules (such as a microRNA or mRNA), a reduction or downregulation refers to any process which results in a decrease in production of a gene product. In the context of the present disclosure, a gene product can be a primary transcript microRNA (pri-miRNA), precursor microRNA (pre-miRNA), or mature microRNA. Gene downregulation includes any detectable decrease in the production of a microRNA. In certain examples, production of a microRNA decreases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Detecting: To identify the existence, presence, or fact of something. General methods of detecting are known to the skilled artisan and may be supplemented with the protocols and reagents disclosed herein. For example, included herein are methods of detecting gene expression in a sample or a subject.

Determining or detecting the level of expression of a gene product: Detection of a level of expression in either a qualitative or quantitative manner, for example by detecting nucleic acid molecules or proteins, for instance using routine methods known in the art.

Diagnosis: The process of identifying a disease, such as muscular dystrophy, by its signs, symptoms and results of various tests. The conclusion reached through that process is also called "a diagnosis." Forms of testing commonly performed include blood tests, medical imaging, urinalysis, and biopsy.

Diagnostically significant amount: As used herein a "diagnostically significant amount" refers to an increase or decrease in the level of a miR gene product in a biological sample that is sufficient to allow one to distinguish one patient population from another (such as a subject with muscular dystrophy from a subject without muscular dystrophy). In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control. A diagnostically significant amount can also be determined by calculating the fold-change in expression of a particular miR between two sample types. Microarray analysis is provided herein as one example of how miR gene product expression can be detected. However, one of skill in the art will recognize that other methods exist to measure gene expression (such as one of the methods described herein) and variation in detected expression levels can occur depending on the method that is used. Thus, the diagnostically significant amount may vary if another method of detection is used, such as RT-PCR.

Effective amount: An amount of agent that is sufficient to generate a desired response, such as reducing or inhibiting one or more signs or symptoms associated with a condition or disease. When administered to a subject, a dosage will generally be used that will achieve target tissue/cell concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example anti-pathogenic agents), induces the desired response such as treatment of a muscular dystrophy, such as DMD, FCMD or MDC1A.

In particular examples, it is an amount of an agent capable of decreasing miRNA-124 expression or activity by least 20%, at least 50%, at least 60%, at least 70%, at least 80%, at least 90%, at least 95%, at least 98%, or even at least 100% (elimination of the disease to a point beyond detection) and/or increasing miRNA-29 expression or activity by least 20%, at least 50%, at least 60%, at least 70%, at least 80%, at least 90%, at least 95%, at least 98%, or even at least 100% (elimination of the disease to a point beyond detection).

In some examples, an effective amount is an amount of a pharmaceutical preparation that alone, or together with a pharmaceutically acceptable carrier or one or more additional therapeutic agents, induces the desired response.

In one example, a desired response is to increase the subject's survival time by slowing the progression of the disease, such as slowing the progression of muscular dystrophy. The disease does not need to be completely inhibited for the pharmaceutical preparation to be effective. For example, a pharmaceutical preparation can decrease the progression of the disease by a desired amount, for example by at least 20%, at least 50%, at least 60%, at least 70%, at least 80%, at least 90%, at least 95%, at least 98%, or even at least 100%, as compared to the progression typical in the absence of the pharmaceutical preparation.

In another or additional example, it is an amount sufficient to partially or completely alleviate symptoms of the muscular dystrophy within the subject. Treatment can involve only slowing the progression of the disease temporarily, but can also include halting or reversing the progression of the disease permanently.

Effective amounts of the agents described herein can be determined in many different ways, such as assaying for a reduction in of one or more signs or symptoms associated with the muscular dystrophy in the subject or measuring the expression level of one or more molecules known to be associated with the muscular dystrophy. Effective amounts also can be determined through various in vitro, in vivo or in situ assays, including the assays described herein.

The disclosed therapeutic agents can be administered in a single dose, or in several doses, for example daily, during a course of treatment. However, the effective amount can be dependent on the source applied (for example a nucleic acid molecule isolated from a cellular extract versus a chemically synthesized and purified nucleic acid), the subject being treated, the severity and type of the condition being treated, and the manner of administration.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, expression, such as expression of miRNA-124 and/or miRNA-29, can be regulated to treat one or more signs or symptoms associated with muscular dystrophy.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have muscular dystrophy, such as DMD, FCMD or MDC1A) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

Extracellular matrix: An extracellular structure of a tissue or a layer thereof, including the arrangement, composition, and forms of one or more matrix components, such as proteins, including structural proteins such as collagen and elastin, proteins such as fibronectin and laminins, and proteoglycans. The matrix may comprise fibrillic collagen, having a network of fibers. In some examples, the extracellular matrix is connected to cells through the costameric protein network.

Increase: To enhance the quality, amount, or strength of something. In one example, an agent increases the activity or expression of an miRNA, such as miRNA-29, for example relative to an absence of the agent. In a particular example, an agent increases the activity or expression of $\alpha 7\beta 1$ by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such increases can be measured using the methods disclosed herein.

In a particular example, a therapy increases (also known as up-regulates) the expression of a miRNA, such as miRNA-29, such as an increase of at least 10%, at least 20%, at least 50%, or even at least 90% in $\alpha 7\beta 1$ expression, thereby treating/alleviating one or more signs or symptoms associated with muscular dystrophy. In certain examples, production of miRNA-29 increases by at least 2-fold, for example at least 3-fold or at least 4-fold, as compared to a control (such an amount of gene expression in a normal cell). In one example, a control is a relative amount of miRNA in a biological sample taken from a subject who does not have muscular dystrophy, such as DMD, FCMD or MDC1A. Such increases can be measured using the methods disclosed herein.

Inhibiting a disease or condition: A phrase referring to reducing the development of a disease or condition, for example, in a subject who is at risk for a disease or who has a particular disease. Particular methods of the present disclosure provide methods for inhibiting muscular dystrophy.

Integrin: A cell surface transmembrane glycoprotein receptor. Integrins are involved in many biological processes such as wound healing, blood clot formation, gene regulation, and immune responses. Integrins can regulate tissue specific cell adhesion molecules. Integrins are heterodimeric non-covalently associated glycoproteins composed of two subunits. The subunits, which are designated a and beta, have approximate molecular weights of 150-180 kilodaltons and 90-110 kilodaltons, respectively.

The α7β1 integrin is a major laminin receptor expressed in skeletal muscle. The α7β1 integrin plays a role in the development of neuromuscular and myotendinous junctions. In the adult, the α7β1 integrin is concentrated at junctional sites and found in extrajunctional regions where it mediates the adhesion of the muscle fibers to the extracellular matrix. Mice that lack the α7 chain develop muscular dystrophy that affects the myotendinous junctions. The absence of α7 integrin results in defective matrix deposition at the myotendinous junction. Loss of the α7 integrin in γ-sarcoglycan mice results in severe muscle pathology. Absence of the α7 integrin in mdx mice also results in severe muscular dystrophy, confirming that the α7β1 integrin serves as a major genetic modifier for Duchenne and other muscular dystrophies.

Mutations in the α7 gene are responsible for muscular dystrophy in humans. A screen of 117 muscle biopsies from patients with undefined muscle disease revealed 3 which lacked the α7 integrin chain and had reduced levels of β1D integrin chain. These patients exhibited delayed developmental milestones and impaired mobility consistent with the role for the α7β1 integrin in neuromuscular and myotendinous junction development and function.

Several lines of evidence suggest the α7 integrin may be important for muscle regeneration. For example, during embryonic development, the α7β1 integrin regulates myoblast migration to regions of myofiber formation. It has been found that MyoD (myogenic determination protein) transactivates α7 integrin gene expression in vitro, which would increase α7 integrin levels in activated satellite cells. Human, mouse and rat myoblast cell lines derived from satellite cells express high levels of α7 integrin. Elevated α7 integrin mRNA and protein are detected in the skeletal muscle of 5 week old mdx mice, which correlates with the period of maximum muscle degeneration and regeneration. In addition, the α7β1 integrin associates with muscle specific β1-integrin binding protein (MIBP), which regulates laminin deposition in C2C12 myoblasts. Laminin provides an environment that supports myoblast migration and proliferation. Finally, enhanced expression of the α7 integrin in dystrophic skeletal muscle results in increased numbers of satellite cells.

The sequences for α7β1 integrin subunits are publicly available on GenBank, see, for example Gene Accession No. NM_001144116 (human) and NM_008398.2 (mouse) for α7 integrin, and Gene Accession No. NM_002211 for β1 integrin (also known as CD29), each of which is herein incorporated by reference as available on Apr. 18, 2014.

A α7β1 integrin-associated condition is a condition associated with altered α7β1 integrin expression or activity, including muscular dystrophy, such as DMD, FCMD, LGMD, FHMD, Beckers muscular dystrophy and/or MDC1A.

Laminin: Any of the family of glycoproteins that are typically involved in the formation and maintenance of extracellular matrices. Laminin is a heterotrimers formed from an a chain, a β chain, and a γ chain. The various chains of a particular laminin can affect the properties of the molecule. In some aspects of the present disclosure, fragments, derivatives, or analogs of various laminins can be used, such as laminins having at least a portion at least substantially homologous to the laminin α1 chain. A "fragment of laminin," as used herein, refers to a portion of a substance, such as laminin. A fragment may be, in some examples, a particular domain or chain of a protein. For example, particular embodiments of the present disclosure involve administering a fragment of laminin-1 corresponding to at least a portion of (or all of) the laminin α1 chain. Fragments may be synthetic or may be derived from larger parent substances.

In some aspects, laminins may be administered as a mixture of laminins, including fragments, analogs, and derivatives thereof. Suitable methods for preparing analogs of laminin domains are disclosed in U.S. Pat. No. 6,933,280, incorporated by reference herein to the extent not inconsistent with this disclosure.

The laminin materials or compositions of the present disclosure may be delivered as discrete molecules or may be complexed with, or conjugated to, another substance. For example, the laminin may be combined with a carrier, such as to aid in delivery of the laminin to a site of interest or to increase physiological uptake or incorporation of the laminin.

In specific examples, the laminin administered includes or consists of laminin-1 (LAM-111), which includes the chains α1β1γ1. In further examples, the laminin administered includes or consists of laminin-2, which includes the chains α2β1γ1. In yet further examples, the laminin administered includes or consists of laminin-4, which includes the chains α2β2γ1.

Laminins may be obtained from any suitable source. For example, laminin-1 may be obtained from placental tissue or from Engelbreth-Holm-Swarm murine sarcoma. Suitable methods of isolating various laminins are disclosed in U.S. Pat. No. 5,444,158, incorporated by reference herein to the extent not inconsistent with the present disclosure.

Measuring or detecting the level of expression: As used herein, measuring or detecting the level of expression of a particular miR or mRNA refers to quantifying the amount of the miR or mRNA present in a sample. Quantification can be either numerical or relative. Detecting expression of the miR or mRNA can be achieved using any method known in the art or described herein, such as by RT-PCR. Detecting expression of a miR or mRNA includes detecting expression of either a mature form of the miR or a precursor form (i.e., a pri-miRNA or pre-miRNA) that is correlated with expression of the miR. Typically, miR detection methods involve sequence specific detection, such as by RT-PCR. miR-specific primers and probes can be designed using the precursor and mature miR nucleic acid sequences that are known in the art (the miRBase microRNA database is available online by the University of Manchester at mirbase.org).

In primary embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal (in that they are not altered for the desired characteristic, for example a sample from a subject who does not have cancer, such as ACC) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

In some embodiments of the methods, the increase or decrease is of a diagnostically significant amount, which refers to a change of a sufficient magnitude to provide a statistical probability of the diagnosis.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). The term "microRNA gene product" includes pri-miRNAs, pre-miRNAs and mature microRNAs (including minor mature miRNA species referred to as miR*). MicroRNAs modulate gene expression by promoting cleavage of target mRNAs or by blocking translation of the cellular transcript. Human microRNAs are referred to as hsa-miR. As microRNAs are identified, researchers register the sequences prior to publication of their work to ensure that each unique microRNA is assigned an official number (the miRBase Registry is available online through the University of Manchester at mirbase.org), eliminating any ambiguity in the literature regarding the identity of particular microRNAs. All miRs referred to by their miRBase registry numbers are herein incorporated by reference as they appear in the miRBase registry as of the filing date of this application. The miRBase registry also provides sequence information for known miRs. The sequence for miRNA-124 is publically available at the miRBase registry, as MI0000443 (hsa-miR-124-1, MI0000444 (hsa-miR-124-2), MI0000445 (hsa-miR-124-3) (human) and MI0000716 (mmu-miR-124-1), MI0000717 (mmu-miR-124-2), MI0000716 (mmu-miR-124-3 (mouse) which is hereby incorporated by reference as available on Apr. 18, 2014. The sequence for miRNA-29 is publically available at the miRBase registry, MI0000087 (hsa-miR-29a), MI0000105 (hsa-miR-29b-1), MI0000107 (hsa-miR-29b-2), MI0000735 (has-miR-29c) (human) and MI0000576 (mmu-miR-29a), MI0000143 (mmu-miR-29b1), MI0000577 (mmu-miR-29c) (mouse), which is hereby incorporated by reference as available on Apr. 18, 2014.

Muscle: Any myoblast, myocyte, myofiber, myotube or other structure composed of muscle cells. Muscles or myocytes can be skeletal, smooth, or cardiac. Muscle may also refer to, in particular implementations of the present disclosure, cells or other materials capable of forming myocytes, such as stem cells and satellite cells.

Muscular dystrophy: A term used to refer to a group of genetic disorders that lead to progressive muscle weakness. Muscular dystrophy can result in skeletal muscle weakness and defects in skeletal muscle proteins, leading to a variety of impaired physiological functions. No satisfactory treatment of muscular dystrophy exists. Existing treatments typically focus on ameliorating the effects of the disease and improving the patient's quality of life, such as through physical therapy or through the provision of orthopedic devices.

Mutated genes associated with muscular dystrophy are responsible for encoding a number of proteins associated with the costameric protein network. Such proteins include laminin-2, collagen, dystroglycan, integrins, caveolin-3, ankyrin, dystrophin, α-dystrobrevin, vinculin, plectin, BPAG1b, muscle LIM protein, desmin, actinin-associated LIM protein, α-actin, titin, telethonin, cypher, myotilin, and the sarcoglycan/sarcospan complex.

The most common form of muscular dystrophy is DMD, affecting 1 in 3,500 live male births. DMD is an X-linked recessive disorder characterized by a mutation in the gene that codes for dystrophin. Dystrophin is a cytoskeletal protein about 430 kDa in size. This protein works to connect the cell's cytoskeleton and extracellular matrix. The loss of dystrophin in DMD patients leads to a loss of muscle fiber attachment at the extracellular matrix during contraction, which ultimately leads to progressive fiber damage, membrane leakage and a loss of muscle function. Most patients die before they reach the age of 30 due to respiratory or cardiac failure.

Beckers muscular dystrophy (also known as Benign pseudohypertrophic muscular dystrophy) is related to DMD in that both result from a mutation in the dystrophin gene, but in DMD no functional dystrophin is produced making DMD much more severe than BMD. BMD is an X-linked recessive inherited disorder characterized by slowly progressive muscle weakness of the legs and pelvis. BMD is a type of dystrophinopathy, which includes a spectrum of muscle diseases in which there is insufficient dystrophin produced in the muscle cells, results in instability in the structure of muscle cell membrane. This is caused by mutations in the dystrophin gene, which encodes the protein dystrophin. The pattern of symptom development of BMD is similar to DMD, but with a later, and much slower rate of progression.

Congenital muscular dystrophies are caused by gene mutations. FCMD and MDC1A are examples of congenital muscular dystrophies. MDC1A is a congential muscular dystrophy due to a genetic mutation in the LAMA2 gene which results in lack of or complete loss of laminin-α2 protein. This loss of laminin-α2 leads to an absence of laminins-211/221. Laminins-211/221 are major components of the extracellular matrix and play a key role in muscle cell development. During muscle cell differentiation laminin binds to the α7β1 integrin. Without laminin-α2, muscle fibers are unable to adhere to the basement membrane and myotubes undergo apotosis. Muscle regeneration also fails, leading to a loss of muscle repair and an increase in muscle fibrosis and inflammation. This chronic tissue injury is a major cause of morbidity and mortality in MDC1A.

Congenital Muscular Dystrophies (CMD) and Limb-Girdle muscular dystrophy (LGMD) are common forms of highly heterogeneous muscular dystrophies which can be distinguished by their age at onset. In CMD, onset of symptoms is at birth or within the first 6 months of life; in LGMD onset of symptoms is in late childhood, adolescence or even adult life. Inheritance in LGMD can be autosomal dominant (LGMD type 1) or autosomal recessive (LGMD type 2), CMD is recessively inherited. CMD and LGMD can overlap both clinically and genetically MDC1A is a progressive muscle wasting disease that results in children being confined to a wheelchair, requiring ventilator assistance to breathe and premature death. Symptoms are detected at birth with poor muscle tone and "floppy" baby syndrome. DMD, BMD and LGMD are progressive muscle degenerative diseases usually diagnosed at 3-5 years of age when children show developmental delay including ability to walk and climb stairs. The disease is progressive and children are usually confined to a wheelchair in their teens and require ventilator assistance.

Fukuyama congenital muscular dystrophy (FCMD) is an inherited condition that predominantly affects the muscles, brain, and eyes. Congenital muscular dystrophies are a group of genetic conditions that cause muscle weakness and wasting (atrophy) beginning very early in life. Fukuyama congenital muscular dystrophy affects the skeletal muscles, which are muscles the body uses for movement. The first signs of the disorder appear in early infancy and include a weak cry, poor feeding, and weak muscle tone (hypotonia). Weakness of the facial muscles often leads to a distinctive facial appearance including droopy eyelids (ptosis) and an open mouth. In childhood, muscle weakness and joint deformities (contractures) restrict movement and interfere with the development of motor skills such as sitting, standing, and walking. Fukuyama congenital muscular dystrophy also impairs brain development. People with this condition have a brain abnormality called cobblestone lissencephaly, in which the surface of the brain develops a bumpy, irregular appearance (like that of cobblestones). These changes in the structure of the brain lead to significantly delayed development of speech and motor skills and moderate to severe intellectual disability. Social skills are less severely impaired. Most children with Fukuyama congenital muscular dystrophy are never able to stand or walk, although some can sit without support and slide across the floor in a seated position. More than half of all affected children also experience seizures. Other signs and symptoms of Fukuyama congenital muscular dystrophy include impaired vision, other eye abnormalities, and slowly progressive heart problems after age 10. As the disease progresses, affected people may develop swallowing difficulties that can lead to a bacterial lung infection called aspiration pneumonia. Because of the serious medical problems associated with Fukuyama congenital muscular dystrophy, most people with the disorder live only into late childhood or adolescence.

Fukuyama congenital muscular dystrophy is seen almost exclusively in Japan, where it is the second most common form of childhood muscular dystrophy (after Duchenne muscular dystrophy). Fukuyama congenital muscular dystrophy has an estimated incidence of 2 to 4 per 100,000 Japanese infants.

Fukuyama congenital muscular dystrophy is caused by mutations in the FKTN gene which encodes fukutin. The most common mutation in the FKTN gene reduces the amount of fukutin produced within cells. A shortage of fukutin likely prevents the normal modification of α-dystroglycan, which disrupts that protein's normal function. Without functional α-dystroglycan to stabilize muscle cells, muscle fibers become damaged as they repeatedly contract and relax with use. The damaged fibers weaken and die over time, leading to progressive weakness and atrophy of the skeletal muscles.

Defective α-dystroglycan also affects the migration of neurons during the early development of the brain. Instead of stopping when they reach their intended destinations, some neurons migrate past the surface of the brain into the fluid-filled space that surrounds it. Because Fukuyama congenital muscular dystrophy involves a malfunction of α-dystroglycan, this condition is described as a dystroglycanopathy.

Facioscapulohumeral muscular dystrophy (FHMD) is a form of muscular dystrophy associated with progressive muscle weakness and loss of muscle tissue. Unlike DMD and BMD which mainly affect the lower body, FSHD affects the upper body mainly the face, shoulder and upper arm muscles. However, it can affect muscles around the pelvis, hips, and lower leg. Symptoms for FSHD often do not appear until age 10-26, but it is not uncommon for symptoms to appear much later. In some cases, symptoms never develop. Symptoms are usually mild and very slowly become worse. Facial muscle weakness is common, and may include eyelid drooping, inability to whistle, decreased facial expression, depressed or angry facial expression, difficulty pronouncing words, shoulder muscle weakness (leading to deformities such as pronounced shoulder blades (scapular winging) and sloping shoulders), weakness of the lower, hearing loss and possible heart conditions.

Patient or Subject: A term that includes human and non-human animals. In one example, the patient or subject is a mammal, such as a human. "Patient" and "subject" are used interchangeably herein.

Pharmaceutically acceptable carriers: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more agents, such as one or more agents capable of modulating miRNA activity or expression, such as miRNA-124 and/or miRNA-29 activity or expression.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical agents to be administered can contain minor amounts of non-toxic auxiliary substances, such as wetting or emulsifying agents, preservatives, and One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Signs or symptoms: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting muscular dystrophy, including measuring creatine kinase levels, electromyography (to determine if weakness is caused by destruction of muscle tissue rather than by damage to nerves) immunohistochemistry/immunoblotting/immunoassay (e.g., ELISA) to measure muscular dystrophy-associated molecules, such as α7β1 integrin or PCR to measure miRNA, such as miRNA-124 and/or miRNA-29. In one example, reducing or inhibiting one or more symptoms or signs associated with muscular dystrophy, includes decreasing the activity or expression of miRNA-124 by a desired amount, for example by at least 20%, at least 50%, at least 60%, at least 70%, at least 80%, at least 90%, at least 95%, at least 98%, or even at least 100%, as compared to the activity and/or expression in the absence of the treatment. Symptoms of muscular dystrophy include, but are not limited to, muscle weakness and loss, difficulty running, difficulty hopping, difficulty jumping, difficulty walking, difficulty breathing, fatigue, skeletal deformities, muscle deformities (contractions of heels; pseudohypertrophy of calf muscles), heart disease (such as dilated cardiomyopathy), elevated creatine phosphokinase (CK) levels in blood or combinations thereof.

Small interfering RNA (siRNA): A double-stranded nucleic acid molecule that modulates gene expression through the RNAi pathway (see, for example, Bass, Nature 411:428-9, 2001; Elbashir et al., Nature 411:494-8, 2001; and PCT Publication Nos. WO 00/44895; WO 01/36646; WO 99/32619; WO 00/01846; WO 01/29058; WO 99/07409; and WO 00/44914). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs," "small interfering RNAs" or "short inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of a miR gene product.

Tissue: An aggregate of cells, usually of a particular kind, together with their intercellular substance that form one of the structural materials of an animal and that in animals include connective tissue, epithelium, muscle tissue, and nerve tissue.

Treating a disease: A therapeutic intervention that ameliorates a sign or symptom of a disease or pathological condition related to a muscular dystrophy, such as a sign or symptom of muscular dystrophy. Treatment can induce remission or cure of a condition or slow progression, for example, in some instances can include inhibiting the full development of a disease, for example preventing development of a muscular dystrophy. Prevention of a disease does not require a total absence of disease. For example, a decrease of at least 50% can be sufficient.

Treating a disease can be a reduction in severity of some or all clinical symptoms of the disease or condition, a reduction in the number of relapses of the disease or condition, an improvement in the overall health or well-being of the subject, by other parameters well known in the art that are specific to the particular disease or condition, and combinations of such factors.

Upregulated or activated: When used in reference to the expression of a nucleic acid molecule (such as a microRNA or mRNA), refers to any process which results in an increase in production of a gene product. In the context of the present disclosure, a gene product can be a primary transcript microRNA (pri-miRNA), precursor microRNA (pre-miRNA), a mature microRNA, mRNA, rRNA, tRNA, structural RNA or protein. Gene upregulation or activation includes any detectable increase in any of these molecules. In certain examples, production of a microRNA increases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control. In some examples, a control is a relative amount of microRNA expression in one or more subjects who do not have muscular dystrophy.

Under conditions sufficient for: A phrase that is used to describe any environment that permits the desired activity. In one example, includes administering a disclosed agent to a subject sufficient to allow the desired activity. In particular examples, the desired activity is altering the expression or activity of miRNA-124 and/or miRNA-29.

II. Methods of Use i. Methods of Treating Muscular Dystrophy

Methods are disclosed herein for treating muscular dystrophy, such as DMD, FCMD, LGMD, FHMD, BMD, MDC1A or MDC1D. In one example, the method includes administering an effective amount of a miR gene product modulatory agent to a subject with muscular dystrophy or suspected of having or developing muscular dystrophy, in which the agent decreases the biological activity or expression of a miR gene product that is up-regulated, such as miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3), in the subject with muscular dystrophy as compared to the control, thereby treating the muscular dystrophy in the subject. In one example, the method includes administering an effective amount of a miR gene product modulatory agent to a subject with muscular dystrophy or suspected of having or developing muscular dystrophy, in which the agent decreases the biological activity or expression of a miR gene product that is miRNA-124-1 and/or 124-2. In other examples, the method includes administering an effective amount of a miR gene product modulatory agent to a subject with muscular dystrophy or suspected of having or developing muscular dystrophy, in which the agent decreases the biological activity or expression of a miR gene product that is miRNA-124-2 and/or 124-3. In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-124-1 and/or 124-3. In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-124-1. In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-124-2. In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-124-3.

In some examples, the method includes administering an effective amount of a miR gene product modulatory agent to a subject with muscular dystrophy or suspected of having or developing muscular dystrophy, in which the agent increases the biological activity or expression of a miR gene product that is down-regulated, such as miRNA-29a, miRNA-29b, and/or miRNA-2c (e.g., hsa-miR-29a, hsa-miR-29b-1, hsa-miR-29b-2, has-miR-29c, mmu-miR-29a, mmu-miR-29b1, and/or mmu-miR-29c), in the subject with muscular dystrophy as compared to a control, thereby treating the muscular dystrophy in the subject. In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29a, miRNA-29b, and/or miRNA-2c. In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29a and/or miRNA-29b (such as miRNA-29b-1 or miRNA-29b-2).

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29b (such as miRNA-29b-1 or miRNA-29b-2) and/or miRNA-29c.

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29a and/or miRNA-29c.

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29a.

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29b-1 and/or miRNA-29b-2.

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29b-1.

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29b-2.

In some examples, the method includes administering an effective amount of a miR gene product modulatory agent to a subject with muscular dystrophy or suspected of having or developing muscular dystrophy, in which the agent increases the biological activity or expression of a miR gene product that is miRNA-29c.

In some examples, the method includes administering an effective amount of a miR gene product modulatory agent to a subject with muscular dystrophy or suspected of having or developing muscular dystrophy, in which the agent decreases the biological activity or expression of a miR gene product that is up-regulated, such as miRNA-29a, miRNA-29b-1, miRNA-29b-2, and/or miRNA-2c (e.g., hsa-miR-29a, hsa-miR-29b-1, hsa-miR-29b-2, has-miR-29c, mmu-miR-29a, mmu-miR-29b1, and/or mmu-miR-29c), in the subject with muscular dystrophy as compared to a control, thereby treating the muscular dystrophy in the subject. In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29a, miRNA-29b-1, miRNA-29b-2, and/or miRNA-2c. In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29a and/or miRNA-29b (such as miRNA-29b-1 or miRNA-29b-2).

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29b (such as miRNA-29b-1 or miRNA-29b-2) and/or miRNA-29c.

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29a and/or miRNA-29c.

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29a.

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29b-1 and/or miRNA-29b-2.

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29b-1.

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29b-2.

In some examples, the method includes administering an effective amount of a miR gene product modulatory agent to a subject with muscular dystrophy or suspected of having or developing muscular dystrophy, in which the agent decreases the biological activity or expression of a miR gene product that is miRNA-29c.

In some example, the method of treatment inhibits or reduces one or more signs or symptoms associated with muscular dystrophy in the subject. In some examples, the method of treatment includes administering an effective amount of a miR gene product modulatory agent to a subject with muscular dystrophy or suspected of having or developing muscular dystrophy, in which the agent decreases the biological activity or expression of a miR gene product that is up-regulated, such as miRNA-124, in the subject with muscular dystrophy as compared to the control, in combination with administering an effective amount of a miR gene product modulatory agent to a subject with muscular dystrophy or suspected of having or developing muscular dystrophy, in which the agent increases the biological activity or expression of a miR gene product that is down-regulated, such as miRNA-29, in the subject with muscular dystrophy as compared to a control, thereby treating the muscular dystrophy in the subject. In some examples, a combination of agents are administered to subject to decrease the biological activity or expression of miR gene products that are up-regulated, such as miRNA-124 and/or miRNA-29, in the subject with muscular dystrophy as compared to the control, The agent can be any compound, such as a nucleic acid molecule, polypeptide, small molecule or other compound that is capable of inhibiting expression of one or more miR gene products or mRNAs up-regulated and/or down-regulated in a subject with or at risk of acquiring muscular dystrophy. In some embodiments, the agent that inhibits expression of a miR gene product, such as miRNA-124 and/or miRNA-29, is an antisense compound specific for the miR gene product, such as miRNA-124, including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3) and/or miRNA-29, including miRNA-29a, miRNA-29b-1, miRNA-29b-2, and/or miRNA-2c (e.g., hsa-miR-29a, hsa-miR-29b-1, hsa-miR-29b-2, has-miR-29c, mmu-miR-29a, mmu-miR-29b1, and/or mmu-miR-29c) antisense compound. In some examples, the antisense compound is an antisense oligonucleotide, siRNA or ribozyme.

In some embodiments, the miR gene product down-regulated in the subject with muscular dystrophy is miRNA-29. In some examples, administration of the isolated miR gene product comprises administering a vector encoding the miR gene product, such as miRNA-29, including miRNA-29a, miRNA-29b-1, miRNA-29b-2, and/or miRNA-2c (e.g., hsa-miR-29a, hsa-miR-29b-1, hsa-miR-29b-2, has-miR-29c, mmu-miR-29a, mmu-miR-29b1, and/or mmu-miR-29c), such as a plasmid vector or a viral vector. In other embodiments, the isolated miR gene product can be delivered, for example, as naked miR or using a liposomal formulation (e.g., the miR can be encapsulated in a liposome), cationic lipids or a polypeptide carrier.

For the diagnosis and treatment methods disclosed herein, the control can be any suitable control, such as a reference value. For example, the reference value (or values if more than one miR gene product is measured) can be an historical value based on average expression of the miR gene product in a healthy subject (a subject that has not been diagnosed with or suspected of having muscular dystrophy). In some examples, the treatment methods include screening a subject for muscular dystrophy prior to administering a disclosed treatment.

An increase or decrease in the expression or activity does not need to be 100% for the agent to be effective. For example, an agent can alter the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing miRNA expression and activity are known to those of ordinary skill in the art, including those described herein.

In a particular example, the subject is a human.

In additional aspects, the method involves selecting a subject with muscular dystrophy. In some example, a subject is selected for treatment following diagnosing the subject with muscular dystrophy. For example, the method can include diagnosing the subject as suffering from muscular dystrophy, such as DMD, MDC1A, MDC1D, LGMD, DMD, FCMD or FHMD.

Methods of diagnosing a subject with muscular dystrophy are known to those of skill in the art and include, but are not limited to, muscle biopsies and measuring serum creatine kinase levels. Additionally, alterations in biomarker known to be associated with muscular dystrophy, such an increase in miRNA-124 including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3) and/or an alteration in miRNA-29, such as an increase or decrease in miRNA-29 (e.g., miRNA-29a, miRNA-29b-1, miRNA-29b-2, and/or miRNA-29c, such as hsa-miR-29a, hsa-miR-29b-1, hsa-miR-29b-2, has-miR-29c, mmu-miR-29a, mmu-miR-29b1, and/or mmu-miR-29c), may be detected by measuring such levels in serum or urine sample.

In some examples, following the measurement of the expression levels of miRNA, such as miRNA-124 and/or miRNA-29, the assay results, findings, diagnoses, predictions and/or treatment recommendations are recorded and communicated to technicians, physicians and/or patients, for example. In certain embodiments, computers are used to communicate such information to interested parties, such as, patients and/or the attending physicians. The therapy selected for administered is then based upon these results.

In one embodiment, the results and/or related information is communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having muscular dystrophy, such as DMD, LGMD, FHMD, BMD, FCMD, MDC1D or MDC1A, results in the physician treating the subject, such as prescribing one or more agents targeting miRNA-124 and/or miRNA-29 activity or expression for inhibiting or delaying one or more signs and symptoms associated with muscular dystrophy. In additional embodiments, the dose or dosing regimen is modified based on the information obtained using the methods disclosed herein.

ii. Methods of Enhancing Muscle Regeneration, Repair, or Maintenance

Also disclosed are methods of enhancing muscle regeneration, repair or maintenance in a subject. In some examples, the method includes administering an effective amount of a miR gene product modulatory agent, such as an agent capable of modulating miRNA-124, including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3) activity and/or expression, to a subject in need of muscle regeneration, repair or maintenance, wherein the modulatory agent decreases miRNA-124 expression or activity as compared to miRNA-124 expression or activity prior to treatment, thereby enhancing muscle regeneration, repair or maintenance in a subject.

In some examples, the method includes administering an effective amount of a miR gene product modulatory agent, such as an agent capable of modulating miRNA-29, including miRNA-29a, miRNA-29b-1, miRNA-29b-2, and/or miRNA-29c (e.g., hsa-miR-29a, hsa-miR-29b-1, hsa-miR-29b-2, has-miR-29c, mmu-miR-29a, mmu-miR-29b1, and/or mmu-miR-29c) activity and/or expression, to a subject in need of muscle regeneration, repair or maintenance, wherein the modulatory agent decreases miRNA-29 expression or activity as compared to miRNA-29 expression or activity prior to treatment, thereby enhancing muscle regeneration, repair or maintenance in a subject.

In some examples, the method includes administering an effective amount of a miR gene product modulatory agent to a subject in need of muscle regeneration, repair or maintenance, in which the agent increases the biological activity or expression of a miR gene product that is down-regulated, such as miRNA-29, including miRNA-29a, miRNA-29b-1, miRNA-29b-2, and/or miRNA-29c (e.g., hsa-miR-29a, hsa-miR-29b-1, hsa-miR-29b-2, has-miR-29c, mmu-miR-29a, mmu-miR-29b1, and/or mmu-miR-29c), in the subject with muscular dystrophy as compared to miRNA-29 expression or activity prior to treatment, thereby enhancing muscle regeneration, repair or maintenance in a subject. In some examples, the method of treatment includes administering an effective amount of a miR gene product modulatory agent to a subject in need of muscle regeneration, repair or maintenance, in which the agent decreases the biological activity or expression of a miR gene product that is up-regulated, such as miRNA-124, including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3) in the subject in need of enhancing muscle regeneration, repair or maintenance as compared to the control or prior to treatment, in combination with administering an effective amount of a miR gene product modulatory agent to the subject which increases the biological activity or expression of a miR gene product that is down-regulated, such as miRNA-29, in the subject, thereby enhancing muscle regeneration, repair or maintenance in a subject.

An increase or decrease in the expression or activity does not need to be 100% for the agent to be effective. For example, an agent can alter the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing miRNA expression and activity are known to those of ordinary skill in the art, including those described herein.

Muscle regeneration may benefit, for example, geriatric or other patient populations with reduced muscle repair capability, or simply speed the muscle repair process for otherwise physiologically unimpaired patients. In particular implementations, administration of a miRNA-124 and/or miRNA-29 modulatory agent can aid muscle repair, or reduction of muscle damage, in athletes or others having activity-induced muscle injury or damage. In yet further implementations, muscle repair in patients suffering from muscle damage, such as through accident or injury, can be augmented by administration of a miRNA-124 and/or miRNA-29 modulatory agent.

In some examples, miRNA-124 and/or miRNA-29 modulatory agents are administered prior to the subject experiencing muscle damage or disease. In some examples, miRNA-124 and/or miRNA-29 modulatory agents are administered to the subject prior to the subject exercising.

In some examples, the method further includes selecting a subject in need of enhancing muscle regeneration, repair, or maintenance. For example, in some instances, selecting a subject in need of enhancing muscle regeneration, repair, or maintenance comprises diagnosing the subject with a condition characterized by impaired muscle regeneration prior to administering an effective amount of a miRNA-124 and/or miRNA-29 modulatory agent to the subject. Methods for diagnosing and selecting a subject in need of muscle regeneration, repair or maintenance are known to those of ordinary skill in the art and include those provided described herein (including those in the Methods of Treatment of Muscular Dystrophy). As stated above, subjects may be selected based upon their life style (e.g., engaged in moderate to intense exercise or physical activities), age (e.g., elderly population at more risk of experiencing muscle degeneration or injury) or pre-disposition to muscle degeneration or injury (e.g., genetics or previous muscle injury).

iii. Methods of Prospectively Preventing or Reducing Muscle Injury or Damage

Also disclosed are methods prospectively preventing or reducing muscle injury or damage in a subject. In some examples, the method includes administering an effective amount of a miR gene product modulatory agent, such as an agent capable of modulating miRNA-124 activity and/or expression, to a subject in which preventing or reducing muscle injury or damage is desired, wherein the modulatory agent decreases miRNA-124, including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3) expression or activity as compared to a reference value or control, such as miRNA-124, including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3) expression or activity prior to the activity, thereby preventing or reducing muscle injury or damage in a subject. In some examples, the method includes administering an effective amount of a miR gene product modulatory agent to a subject in which preventing or reducing muscle injury or damage is desired, in which the agent increases the biological activity or expression of a miR gene product that is down-regulated, such as miRNA-29, including miRNA-29a, miRNA-29b-1, miRNA-29b-2, and/or miRNA-29c (e.g., hsa-miR-29a, hsa-miR-29b-1, hsa-miR-29b-2, has-miR-29c, mmu-miR-29a, mmu-miR-29b1, and/or mmu-miR-29c), in the subject as compared to a reference value or control, such as miRNA-29 expression or activity prior to activity, thereby preventing or reducing muscle injury or damage in a subject. In some examples, the method of treatment includes administering an effective amount of a miR gene product modulatory agent to a subject in need of muscle regeneration, repair or maintenance, in which the agent decreases the biological activity or expression of a miR gene product that is up-regulated, such as miRNA-124, in the subject in which preventing or reducing muscle injury or damage is desired as compared to the control or prior to treatment, in combination with administering an effective amount of a miR gene product modulatory agent to the subject which increases the biological activity or expression of a miR gene product that is down-regulated, such as miRNA-29, in the subject, thereby preventing or reducing muscle injury or damage in a subject.

An increase or decrease in the expression or activity does not need to be 100% for the agent to be effective. For example, an agent can alter the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing miRNA expression and activity are known to those of ordinary skill in the art, including those described herein.

In some examples, the method further includes selecting a subject at risk for developing a muscle injury or damage. In some examples, the miRNA-124 and/or miRNA-29 modulatory agent is administered to a subject prior to the subject exercising.

In some examples, the method further includes selecting a subject at risk for developing a muscle injury or damage. Methods for selecting such s subject are known to those of ordinary skill in the art and include those provided described herein. As stated above, subjects may be selected based upon their life style (e.g., engaged in moderate to intense exercise or physical activities), age (elderly population at more risk of experiencing muscle degeneration or injury) or predisposition to muscle degeneration or injury (e.g., genetics or previous muscle injury).

iv. Methods of Enhancing α7⊕1 Integrin Expression

Also disclosed herein are methods of enhancing α7β1 integrin expression. In some examples, these methods include contacting a cell with an effective amount of a miRNA-124, including miRNA-124-1, 124-2 and/or 124-3 (e.g., up-regulated hsa-miR-124-1, hsa-miR-124-2, hsa-miR-124-3, mmu-miR-124-1, mmu-miR-124-2, and/or mmu-miR-124-3), and/or miRNA-29, including miRNA-29a, miRNA-29b-1, miRNA-29b-2, and/or miRNA-29c (e.g., hsa-miR-29a, hsa-miR-29b-1, hsa-miR-29b-2, has-miR-29c, mmu-miR-29a, mmu-miR-29b1, and/or mmu-miR-29c), modulatory agent, and increases in α7β1 integrin expression in the treated cell relative to α7β1 integrin expression in an untreated cell, indicates the agent is capable of enhancing α7β1 integrin expression. In some examples, the cell is a muscle cell, such as a skeletal muscle cell. In some examples, the muscle cell is present in a mammal, and wherein contacting the cell with an agent comprises administering the agent to the mammal. In some examples, the disclosed α7β1 integrin modulatory agents can increase the expression of nucleic acid sequences (such as DNA, cDNA, mRNAs, or miRNAs) and proteins of α7β1 integrin. An increase in the expression or activity does not need to be 100% for the agent to be effective. For example, an agent can increase the expression or biological activity by a desired amount, for example by at least 10%, for example at least 20%, at least 50%, at least 60%, at least 70%, at least 80%, at least 90%, at least 95%, at least 98%, or even at least 100%, including about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in a control. Methods of assessing α7β1 integrin expression and activity are known to those of ordinary skill in the art, including those described herein (e.g., Western blot and ELISA assay with commercially available antibodies).

iv. Diagnostic Methods

Provided herein is a method of diagnosing a subject as having muscular dystrophy as described herein by measuring the level of at least one microRNA (miR) gene product in a biological sample of the subject. In particular embodiments, at least one miR gene product is miRNA-124, including miRNA-124-1, 124-2 and/or 124-3 (e.g., hsa-miR-124-1, hsa-miR-124-2, hsa-miR-124-3, mmu-miR-124-1, mmu-miR-124-2, and/or mmu-miR-124-3) or miRNA-29, including miRNA-29a, miRNA-29b-1, miRNA-29b-2, and/or miRNA-29c (e.g., hsa-miR-29a, hsa-miR-29b-1, hsa-miR-29b-2, has-miR-29c, mmu-miR-29a, mmu-miR-29b1, and/or mmu-miR-29c). An alteration in the level of the at least one miR gene product or mRNA in the biological sample of the subject relative to a control indicates the subject has the disorder. In particular embodiments, an increase in the amount of miRNA-124 and/or a decrease in the amount of miRNA-29 in a biological sample obtained from a subject relative to a control, indicates the subject has or at risk of developing muscular dystrophy. In particular embodiments, an increase in the amount of miRNA-124 and/or a increase in the amount of miRNA-29 in a biological sample obtained from a subject relative to a control, indicates the subject has or at risk of developing muscular dystrophy. In some embodiments, the increase or decrease in the level of the miRNA is of a diagnostically significant amount.

In some embodiments of the methods, the diagnostically significant increase or decrease in expression of the miR gene product is at least 2-fold, such as at least 3-fold, at least 4-fold, at least 5-fold, at least 10-fold, including about 3-fold, about 4-fold, about 5-fold, about 6-fold, about 7-fold, about 8-fold, about 9-fold, about 10-fold, about 30-fold, and about 100-fold. In particular examples, miRNA-124 is increased by at least 2-fold in the biological sample of the subject relative to the control. In particular examples, miRNA-29 is decreased by at least 2-fold in the biological sample of the subject relative to the control. In particular examples, miRNA-29 is increased by at least 2-fold in the biological sample of the subject relative to the control.

Methods of detecting and measuring miRNA expression are well known in the art and are described in detail below. In some examples, RT-PCR is used to measure the level of a miRNA, such as when a single miRNA is analyzed. In other cases, when multiple miR gene products are to be measured, it may be desirable to use microarray analysis.

The miR gene product measured can be a primary miRNA (pri-miRNA) precursor miRNA (pre-miRNA), or a mature miRNA (including minor mature miRNA products).

In some embodiments of the methods, the biological sample is blood, or a component thereof, such as plasma or serum. Thus, the method in some examples includes obtaining an appropriate sample from the patient to be diagnosed or treated with the methods provided herein.

In some embodiments, the method further includes providing an appropriate therapy for the subject diagnosed with muscular dystrophy as described in detail herein. In some examples, the therapy includes administering an agent that inhibits expression of a miR gene product, such as an agent that inhibits a miR gene product identified as up-regulated in muscular dystrophy, such as miRNA-124. In other examples, the therapy includes administering an agent that includes administering an isolated miR gene product, such a miR gene product that has been identified as down-regulated, such as miRNA-29, relative to a control.

In some embodiments, a patient suspected of having muscular dystrophy, can be pre-selected for the treatment and screening methods herein.

In some embodiments, once a patient's diagnosis is determined, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

In other examples, the output is a numerical value, such as an amount of one or more miRNAs (e.g., and amount of expression of the miRNAs compared to a control or reference value), such as miRNA-124 and/or miRNA-29 expression in the sample or a relative amount of miRNA-124 and/or miRNA-29 expression in the sample as compared to a control. In additional examples, the output is a graphical representation, for example, a graph that indicates the value (such as amount or relative amount) of one or more miRNAs, such as miRNA-124 and/or miRNA-29, expression in the sample from the subject on a standard curve. In a particular example, the output (such as a graphical output) shows or provides a cut-off value or level that indicates the presence of digestive or liver disorder. In some examples, the output is communicated to the user, for example by providing an output via physical, audible, or electronic means (for example by mail, telephone, facsimile transmission, email, or communication to an electronic medical record).

The output can provide quantitative information (for example, an amount of one or more miRNAs, e.g., miRNA-124 and miRNA-29, expression relative to a control sample or value) or can provide qualitative information (for example, a diagnosis of a digestive or liver disorder). In additional examples, the output can provide qualitative information regarding the relative amount of one or more miRNAs, such as miRNA-124 and miRNA-29.

In some examples, the output is accompanied by guidelines for interpreting the data, for example, numerical or other limits that indicate the presence or absence of metastasis. The guidelines need not specify whether metastasis is present or absent, although it may include such a diagnosis. The indicia in the output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen. In some examples, the test may include determination of other clinical information (such as determining the amount of one or more additional biomarkers in the sample).

In some embodiments, the disclosed methods of diagnosis include one or more of the following depending on the patient's diagnosis: a) prescribing a treatment regimen for the patient if the patient's determined diagnosis is considered to be positive for muscular dystrophy; or b) not prescribing a treatment regimen for the patient if the patient's determined diagnosis is considered to be negative for muscular dystrophy. In an alternative embodiment, the method can include recommending (a) or (b).

MicroRNA Nomenclature and Nucleotide Sequences

MicroRNAs (also known as miRNAs and miRs) are short RNA sequences expressed from longer transcripts found in the genomes of animals, plants and viruses and at least one single-celled eukaryote (Molnar et al., *Nature* 447:1126-1129, 2007; Zhao et al., *Genes Dev.* 21:1190-1203, 2007). MicroRNAs regulate the expression of target genes by binding to complementary sites in the target gene transcripts to cause translational repression or transcript degradation (Pillai et al., *Trends Cell Biol.* 17:118-126, 2007). These small RNA molecules have been implicated in a number of biological processes related to development, cell proliferation, apoptosis, metabolism, morphogenesis and disease (particularly cancer) (Kloosterman and Plasterk, *Dev. Cell* 11:441-450, 2006).

A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs).

A nomenclature scheme has been well established for microRNAs (Griffiths-Jones et al., *Nucleic Acids Res.* 34:D140-D144, 2006; Ambros et al., RNA 9:277-279, 2003; Griffiths-Jones, *Nucleic Acids Res.* 32:D109-D111, 2004). For example, a microRNA name includes a three or four letter species prefix, such as "hsa" for *Homo sapiens*, and a numeric suffix, such as "100," resulting in a complete name of "hsa-miR-100." As used herein, miRNAs not denoted by a specific prefix such as "hsa" can include multiple species, such as human and mouse. Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-124a and miR-124b). In some cases, mature miRNAs from both the 5' and 3' arms of the hairpin precursor are identified, which are designated "3p" or "5p" (such as miR-483-3p and miR-483-5p). Viral microRNA names relate to the locus from which the microRNA is derived (for example, ebv-miR-BART1 is from the Epstein-Ban virus BART locus).

MicroRNA gene product sequences are well described throughout the scientific and patent literature and are available online through miRBase (mirbase.org), provided by the University of Manchester (previously provided by the Sanger Institute). The miRBase registry provides the nucleotide sequences of all published animal, plant and viral microRNAs (Griffiths-Jones et al., *Nucleic Acids Res.* 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR*.

Detecting miRNA and mRNA Expression

As described below, expression of one or more miRNAs associated with muscular dystrophy can be detected using any one of a number of methods well known in the art. In some embodiments of the methods provided herein, microRNA expression profiles are used to diagnose muscular dystrophy and to predict the prognosis and develop potential therapies for patients with muscular dystrophy.

Thus, the disclosed methods can include evaluating miRNA, such as miRNA-124 and miRNA-29. In some examples, the miRNAs are quantified.

The sequences of precursor microRNAs and mature miRNAs are publicly available, such as through the miRBase database, available online by the University of Manchester, and formerly maintained by the Sanger Institute (see Griffiths-Jones et al., *Nucleic Acids Res.* 36:D154-D158, 2008; Griffiths-Jones et al., *Nucleic Acids Res.* 34:D140-D144, 2006; and Griffiths-Jones, *Nucleic Acids Res.* 32:D109-D111, 2004). The sequences of particular mRNAs are also publicly available, such as through GENBANK®.

Detection and quantification of microRNA expression can be achieved by any one of a number of methods well known in the art including those described herein. U.S. Patent Application Publication Nos. 2006/0211000 and 2007/0299030 describe methods of miRNA detection and quantification. Further, general methods for mRNA extraction are well known in the art and are disclosed in standard textbooks of molecular biology, including Ausubel et al., Current Protocols of Molecular Biology, John Wiley and Sons (1997). Using the known sequences for a microRNA of interest, specific probes and primers can be designed for use in the detection methods described herein as appropriate.

In some cases, the microRNA detection method requires isolation of nucleic acid from a sample, such as a cell, biological fluid sample or tissue sample (for example, blood sample). Nucleic acids, including RNA and specifically miRNA or mRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain mRNA, miRNAs and siRNAs.

Microarray analysis of microRNAs can be accomplished according to any method known in the art (see, for example, PCT Publication No. WO 2008/054828; Ye et al., *Nat. Med.* 9(4):416-423, 2003; Calin et al., *N. Engl. J. Med.* 353(17): 1793-1801, 2005). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding microRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing miRNA extracted from a cell, biological fluid or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described herein.

Any one of a number of methods for detecting expression of a gene of interest (including microRNAs) known in the art can be used to detect expression of a microRNA or mRNA. A number of these methods, including qRT-PCR, array, microarray, in situ hybridization, in situ PCR, SAGE are described in further detail below. miRNA detection can also be accomplished by deep sequencing, according to methods known in the art (Creighton et al., *Brief Bioinform.* 10(5): 490-2009 Ma497, 2009).

a. RT-PCR

Methods for quantitating RNA, including microRNA, are well known in the art. In some embodiments, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). However, any suitable reverse transcriptase known in the art can be used for RT-PCR. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif.), following the manufacturer's instructions. The derived cDNA can then be used as a template in the subsequent PCR reaction.

Although the PCR step can use a variety of thermostable DNA-dependent DNA polymerases, it often employs the Taq DNA polymerase, which has a 5'-3' nuclease activity but lacks a 3'-5' proofreading endonuclease activity. TaqMan® PCR typically utilizes the 5'-nuclease activity of Taq or Tth DNA polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, 18S ribosomal RNA and small nucleolar RNA such as U6.

The steps of a representative protocol for quantitating gene expression using fixed, paraffin-embedded tissues as the RNA source, including RNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tissue samples. The RNA is then extracted, and protein and DNA are removed. Alternatively, RNA is located directly from a tissue, cell or fluid sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as a microRNA. Primers that can be used to amplify a particular microRNA or mRNA are commercially available (in some instance) or can be designed and synthesized according to well-known methods using publically available sequences of the microRNA.

b. Serial Analysis of Gene Expression (SAGE)

SAGE is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

c. In Situ Hybridization (ISH)

ISH is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of microRNAs.

Sample cells or tissues are treated to increase their permeability to allow a probe, such as microRNA-specific probe or a mRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a adrenal cortex tissue sample. Since the sequences of the mRNAs of interest are known, probes can be designed accordingly such that the probes specifically bind the gene of interest.

d. In Situ PCR

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

e. Arrays for Profiling MicroRNA Expression

In particular embodiments provided herein, arrays can be used to evaluate microRNA mRNA expression, for example to diagnose or prognose muscular dystrophy. When describing an array that comprises probes or primers specific for a particular set of microRNAs, such an array includes probes or primers specific for miRNA-124 and/or miRNA-29, and can further include control probes (for example to confirm the incubation conditions are sufficient). Exemplary control probes include GAPDH, RNU48, RNU6, actin, and YWHAZ. In one example, an array is a multi-well plate (e.g., 98 or 364 well plate).

In one example, the array includes, consists essentially of, or consists of probes or primers that can recognize miRNA-124 and miRNA-29 and optionally includes RNU48, and RNU6 for the control probe. In some examples, the array includes, consists essentially of, or consists of probes or primers that can recognize miRNA-124 and miRNA-29, optionally including RNU48 or RNU6 (a control probe). The oligonucleotide probes or primers can further include one or more detectable labels, to permit detection of hybridization signals between the probe and target sequence (such as one of the microRNAs disclosed herein).

f. Output of miRNA Gene Expression Analysis Results

Gene expression can be evaluated using any technique described above, or any other method known in the art. As described herein, gene expression can be measured, for example, using labeled probes that can be detected using standard equipment. For example, gene expression measurements using microarray or RT-PCR (which typically use labeled probes specific for a gene product) can be quantitated using a microarray scanner or other suitable scanner for detecting the label. In some embodiments, the device used to measure gene expression is a microarray scanner. Microarray scanners are well known and are commercially available, such as the Model G250GB Microarray Scanner from Agilent Technologies.

The results of gene expression analysis can be transmitted using any one of a number of output devices or formats known in the art. For example, the output device can be a visual output device, such as a computer screen or a printed piece of paper. In other examples, the output device can be an auditory output device, such as a speaker. In other examples, the output device is a printer. In some cases, the data is recorded in a patient's electronic medical record.

Modulating MicroRNA Expression

It is disclosed herein that many microRNAs are differentially expressed in patients with muscular dystrophy or other muscle disorders. As such, an increase in the level of one or more microRNAs down-regulated in patients with muscular dystrophy or other possible muscle disorder, or a decrease in the level of one or more microRNAs up-regulated in patients with muscular dystrophy or muscle disorder may be beneficial for inhibiting the development or progression of muscular dystrophy or other muscle disorder, and/or for alleviating one or more signs or symptoms of muscular dystrophy or other muscle disorder.

a. Use of Agents that Inhibit Up-Regulated MicroRNAs

Provided herein is a method of treating a patient with muscular dystrophy or other muscle disorder (such as a subject in need of enhancing muscle regeneration, repair or maintenance or preventing or reducing muscle damage), by administering to the patient a therapeutically effective amount of an agent that inhibits expression of a miR gene product that is up-regulated in patients with muscular dystrophy or other muscle disorder, such as miRNA-124 and/or miRNA-29, compared with a control.

As used herein, "inhibiting expression of miR gene product" means that the production of the precursor and/or active, mature form of the miR gene product after treatment is less than the amount produced prior to treatment. One skilled in the art can readily determine whether miR expression has been inhibited in a subject, using the techniques known in the art and described herein. Inhibition can occur at the level of gene expression (i.e., by inhibiting transcription of a miR gene encoding the miR gene product) or at the level of processing (e.g., by inhibiting processing of a miR precursor into a mature miR).

A therapeutically effective amount of a compound that inhibits miR expression is an amount sufficient to result in a biological effect (such as alleviating one or more signs or symptoms of muscular dystrophy). For example, an agent can decrease or increase the expression level of a target miR by a desired amount, for example by at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value. In some examples, the therapeutically effective amount is that which results in at least a 2-fold alteration in miRNA-124 and/or miRNA-29.

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject an agent that inhibits expression of miR gene product.

In some embodiments, a single agent that inhibits expression of a miR gene product is administered to the subject in need of treatment. In other embodiments, two or more agents (such as 2, 3, 4, 5, 6, 7, 8, 9 or 10 or more) that inhibit expression of a miR gene product are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

In some embodiments, an agent that inhibits miR expression can be administered to a subject in combination with one or more additional treatments for muscular dystrophy or other muscular disorders.

An agent that inhibits expression of a miR gene product can be any type of compound, such as, but not limited to, a nucleic acid molecule, polypeptide, antibody or small molecule, that is capable of inhibiting expression of one or more miR gene products. In some embodiments, the agent is an antisense compound.

Any type of antisense compound that specifically targets a miR gene product is contemplated for use to inhibit expression of the target miR gene product. In some examples, the agent is an antisense compound selected from an antisense oligonucleotide, a siRNA, or a ribozyme. Methods of designing, preparing and using antisense compounds are within the abilities of one of skill in the art. Furthermore, sequences for the disclosed miR gene products are publicly available. Antisense compounds specifically targeting a miR, such as miRNA-124, that is differentially expressed in muscular dystrophy (or other target nucleic acid) can be prepared by designing compounds that are complementary to the target nucleotide sequence, such as a pri-microRNA, pre-microRNA or mature microRNA sequence. Antisense compounds need not be 100% complementary to the target nucleic acid molecule to specifically hybridize with the target nucleic acid molecule. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003-0228689).

In some embodiments, the antisense compounds are antisense oligonucleotides. The miR gene product-specific antisense oligonucleotides can be any suitable length to allow for hybridization and modulation of gene expression. The length of an antisense oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 29 nucleotides in length, preferably from about 19 to about 25 nucleotides in length, such as about 21 to about 23 nucleotides in length. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target miR gene product. As used herein, an siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally-occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

In other embodiments, the antisense compound is a ribozyme. Ribozymes are nucleic acid molecules having a substrate binding region that is complementary to a contiguous nucleic acid sequence of a miR gene product, and which is able to specifically cleave the miR gene product. The substrate binding region need not be 100% complementary to the target miR gene product. For example, the substrate binding region can be, for example, at least about 50%, at least about 75%, at least about 85%, or at least about 95% complementary to a contiguous nucleic acid sequence in a miR gene product. The enzymatic nucleic acids can also include modifications at the base, sugar, and/or phosphate groups.

Antisense compounds, such as antisense oligonucleotides, siRNAs and ribozymes, can be produced chemically or biologically, or can be expressed from a recombinant plasmid or viral vector, as described in further detail below in regard to expression of isolated miR gene products. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, Science 261:1004, 1993; Werner and Uhlenbeck, Nucl. Acids Res. 23:2092-2096, 1995; Hammann et al., Antisense and Nucleic Acid Drug Dev. 9:25-31).

In some examples, the antisense compounds specific for a miR gene product contain one or more modifications to enhance nuclease resistance and/or increase activity of the compound. Modified antisense compounds include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the oligonucleotide or antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (Science 254, 1497-1500, 1991).

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., Helv. Chim. Acta., 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993).

Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692.

b. Use of Nucleic Acid Molecules Encoding Down-Regulated MicroRNAs

Also provided is a method of treating a patient with muscular dystrophy or other muscle disorder by administering to the patient a therapeutically effective amount of an isolated microRNA gene product that is down-regulated, such as miRNA-29, in a patient with muscular dystrophy or other muscle disorder, relative to a control (such as a healthy subject). As described herein, the miR gene product can be a pri-miRNA, a pre-miRNA or a mature miRNA.

The disclosed methods comprise administering an effective amount of at least one isolated miR gene product, or an isolated variant or biologically-active fragment thereof. The isolated miR gene product that is administered to the subject can be identical to an endogenous wild-type miR gene product (such as a pri-miRNA, pre-miRNA or mature miRNA) that is down-regulated in the patient with muscular dystrophy or other muscle disorder, or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, or inhibiting processing of a target RNA molecule) and inhibition of a cellular process associated with muscular dystrophy or other muscle disorder. These variants include species variants and variants that are the consequence of one or more mutations (e.g., a substitution, a deletion, an insertion) in a miR gene. In certain embodiments, the variant is at least about 70%, at least about 75%, at least about 80%, at least about 85%, at least about 90%, at least about 95%, at least about 98%, or at about 99% identical to a corresponding wild-type miR gene product.

As used herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with muscular dystrophy or other muscle disorder. In certain embodiments, the biologically-active fragment is at least about 9, at least about 11, at least about 13, at least about 15, at least about 17 or at least about 19 nucleotides in length.

A therapeutically effective amount of an isolated gene product can be, for example, the amount necessary to alleviate one or more signs or symptoms of muscular dystrophy or other muscle disorder, and/or the amount required to delay progression of the disease. One of skill in the art can determine the amount of an isolated miR gene product required for therapeutic efficacy.

In some embodiments, a single isolated miR gene product, such as miRNA-29, is administered to the subject in need of treatment. In other embodiments, two or more miR gene products (such as 2, 3, 4, 5, 6, 7, 8, 9 or 10 or more) are administered to the subject. When two or more miR gene products are administered to the subject, the miR gene products can be administered simultaneously (or within quick succession, such as within minutes of each other), or they can be administered at different times. For example, two or more miR gene products can be administered one hour, twelve hours, one day, two days, five days, one week, two weeks or one month apart.

In some embodiments, an isolated miR gene product can be administered to a subject in combination with one or more additional treatments for muscular dystrophy or other muscle disorder. Exemplary muscular dystrophy or other muscle disorder treatments include are known to the person of skill in the art.

As used herein, an "isolated" miR gene product is one that is synthesized, or is purified away from other biological components of the cell or tissue in which the miR naturally occurs. For example, a synthetic miR gene product, or a miR gene product partially or completely separated from the other biological components of its natural state is considered to be "isolated." Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, for example, Proligo (Hamburg, Germany), Dharmacon Research (Lafayette, Co.), Pierce Chemical (Rockford, Ill.), Glen Research (Sterling, VS), ChemGenes (Ashland, Mass.) and Cruachem (Glasgow, United Kingdom).

In some embodiments, the method includes administering a vector encoding a miR gene product. Vectors can be of non-viral (for example, plasmids) or viral (for example, adenovirus, adeno-associated virus, retrovirus, herpes virus, vaccinia virus) origin. Suitable vectors, such as gene therapy vectors, are well known in the art.

In some examples, the miR gene products are expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the invention can also comprise inducible or regulatable promoters for expression of the miR gene products.

When two or more miR gene products are to be expressed, the miR gene products can each be expressed from separate recombinant plasmids, or they can be expressed from the same recombinant plasmid. In one embodiment, the miR gene products are expressed as RNA precursor molecules from a single plasmid, and the precursor molecules are processed into the functional miR gene product within the target cell. Selection of plasmids suitable for expressing the miR gene products, methods for inserting nucleic acid sequences into the plasmid to express the gene products, and methods of delivering the recombinant plasmid to the cells of interest are within the skill in the art (see, for example, Zeng et al., *Mol. Cell* 9:1327-1333, 2002; Tuschl, *Nat. Biotechnol.*, 20:446-448, 2002; Brummelkarnp et al., *Science* 296:550-553, 2002; Miyagishi et al., *Nat. Biotechnol.* 20:497-500, 2002; Paddison et al., *Genes Dev.* 16:948-958, 2002; Lee et al., *Nat. Biotechnol.* 20:500-505, 2002; and Paul et al., *Nat. Biotechnol.* 20:505-508, 2002). In one embodiment, a plasmid expressing the miR gene product comprises a sequence encoding a miR precursor RNA operably linked to the CMV intermediate-early promoter.

The miR gene products can also be expressed from recombinant viral vectors. When administering two or more miR gene products, it is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in target cells or tissues of a patient with the muscular dystrophy or other muscle disorder.

The recombinant viral vectors of use with the disclosed methods include sequences encoding the miR gene products and any suitable promoter for expressing the RNA sequences. Suitable promoters include, but are not limited to, the U6 or H1 RNA pol III promoter sequences, or a cytomegalovirus promoter. Selection of other suitable promoters is within the skill in the art. The recombinant viral vectors of the invention can also comprise inducible or regulatable promoters for expression of the miR gene products.

Suitable viral vectors include, but are not limited to, adenovirus vectors, adeno-associated virus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Zern and Kresinam, *Hepatology* 25(2), 484-491, 1997). Representative adenoviral vectors which can be used for the methods provided herein are described by Stratford-Perricaudet et al. (*J. Clin. Invest.* 90: 626-630, 1992); Graham and Prevec (In *Methods in Molecular Biology: Gene Transfer and Expression Protocols* 7: 109-128, 1991); and Barr et al. (*Gene Therapy*, 2:151-155, 1995).

Adeno-associated virus (AAV) vectors also are suitable for administration of HCC-associated genes. Methods of generating AAV vectors, administration of AAV vectors and their use are well known in the art (see, for example, U.S. Pat. No. 6,951,753; U.S. Pre-Grant Publication Nos. 2007-036757, 2006-205079, 2005-163756, 2005-002908; and PCT Publication Nos. WO 2005/116224 and WO 2006/119458).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well described in the art (see, for example, U.S. Pat. Nos. 6,951,753; 6,379,674; 6,613,892; 6,692,955; 6,344,445; 6,319,703; and 6,261,552; and U.S. Patent Application Publication No. 2003-0083289).

One skilled in the art can readily determine an effective amount of a miR gene product to be administered to a given subject, by taking into account factors, such as the size and weight of the subject; the extent of disease progression; the age, health and sex of the subject; the route of administration; and whether the administration is regional or systemic.

For example, an effective amount of an isolated miR gene product can be based on the approximate body weight of a subject to be treated. Such effective amounts can be administered by any suitable route, such as, for example, parenterally or enterally. In some examples, an effective amount of the isolated miR gene product that is administered to a subject can range from about 5 to about 3000 micrograms/kg of body weight, from about 700 to about 1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

Administration of Agents

Agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some embodiments, the therapeutic agent is a nucleic acid molecule, such as a miR gene product, a vector encoding a miR gene product, an antisense compound or a vector encoding an antisense compound. A nucleic acid-based therapeutic agent can be administered to a subject by any suitable route. In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

In the context of the present disclosure, a miR gene product or an antisense compound can be administered to the subject either as naked RNA or DNA in combination with a delivery reagent, or can be encoded by a recombinant plasmid or viral vector. Recombinant plasmids and viral vectors including sequences that express the miR gene products or antisense compounds, and techniques for delivering such plasmids and vectors to target cells, are well known in the art.

In some embodiments, liposomes are used to deliver a miR gene product or antisense compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a miR gene product or antisense compound to a subject. Cationic lipids and polymers that can be used to deliver therapeutic RNA molecules have been described (see, for example, Zhang et al., *J Control Release.* 123(1):1-10, 2007; Vorhies et al., *Methods Mol Biol.* 480:11-29, 2009; and U.S. Patent Application Publication No. 2009/0306194). Polypeptide carriers can also be used to administer a miR gene product to a subject (see, for example, Rahbek et al., *J. Gene Med.* 10:81-93, 2008).

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the targeted molecule. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Particular dosage regimens can be tailored to a particular subject, condition to be treated, or desired result. For example, when the methods of the present disclosure are used to treat muscular dystrophy or similar conditions, an initial treatment regimen can be applied to arrest the condition. Such initial treatment regimen may include administering a higher dosage of one or more of the disclosed miRNA modulatory agents, or administering such material more frequently, such as daily. After a desired therapeutic result has been obtained, such as a desired level of muscle regeneration, a second treatment regimen may be applied, such as administering a lower dosage of one or more of the disclosed miRNA modulatory agents or administering such material less frequently, such as monthly, bi-monthly, quarterly, or semi-annually. In such cases, the second regimen may serve as a "booster" to restore or maintain a desired level of muscle regeneration. Similar treatment regimens may be used for other subjects with reduced or impaired muscle regeneration capabilities, such as geriatric subjects.

When particular methods of the present disclosure are used to prevent or mitigate muscle damage, such as damage caused by exertion or injury, the subject is typically treated a sufficient period of time before the exertion or injury in order to provide therapeutic effect. For example, the subject may be treated at least about 24 hours before the expected activity or potential injury, such as at least about 48 hours, about 72 hours, about 1 week, about 2 weeks, about three weeks, or about 4 weeks or more prior.

When embodiments of the method of the present disclosure are used to prevent or treat a muscle injury, one or more of the disclosed miRNA modulatory agents or other therapeutic substance can be applied directly to, or proximately to, the area to be treated. For example, the substance can be injected into or near the area. In further examples, the substance can be applied topically to the area to be treated. Treatment is typically initiated prior to the injury to several weeks following the injury. In more specific implementations, the treatment is initiated between about 12 and about 72 hours following injury, such as between about 24 and about 48 hours following injury. In some cases, a single administration of the substance is effective to provide the desired therapeutic effect. In further examples, additional administrations are provided in order to achieve the desired therapeutic effect.

Amounts effective for various therapeutic treatments of the present disclosure may, of course, depend on the severity of the disease and the weight and general state of the subject, as well as the absorption, inactivation, and excretion rates of the therapeutically-active compound or component, the dosage schedule, and amount administered, as well as other factors known to those of ordinary skill in the art. It also should be apparent to one of ordinary skill in the art that the exact dosage and frequency of administration will depend on the particular miRNA modulatory agent, or other therapeutic substance being administered, the particular condition being treated, the severity of the condition being treated, the age, weight, general physical condition of the particular subject, and other medication the subject may be taking. Typically, dosages used in vitro may provide useful guidance in the amounts useful for in vivo administration of the pharmaceutical composition, and animal models may be used to determine effective dosages for treatment of particular disorders. For example, mouse models of muscular dystrophy may be used to determine effective dosages that can then be translated to dosage amount for other subjects, such as humans, as known in the art. Various considerations in dosage determination are described, e.g., in Gilman et al., eds., *Goodman And Gilman's: The Pharmacological Bases of Therapeutics,* 12th ed., Pergamon Press (2010); and *Remington's Pharmaceutical Sciences,* 22nd ed., Mack Publishing Co., Easton, Pa. (2012), each of which is herein incorporated by reference to the extent not inconsistent with the present disclosure.

Desired Response

A desired response refers to an amount effective for lessening, ameliorating, eliminating, preventing, or inhibiting at least one symptom of a disease, disorder, or condition treated and may be empirically determined. In various embodiments of the present disclosure, a desired response is muscle regeneration, reductions or prevention of muscle degeneration, promotion of muscle maintenance, reduction or prevention of muscle injury or damage, reduction or prevention in one more signs or symptoms associated with muscular dystrophy.

In particular, indicators of muscular health, such as muscle cell regeneration, maintenance, or repair, can be assessed through various means, including monitoring markers of muscle regeneration, such as transcription factors such as Pax7, Pax3, MyoD, MRF4, and myogenin. For example, increased expression of such markers can indicate that muscle regeneration is occurring or has recently occurred. Markers of muscle regeneration, such as expression of embryonic myosin heavy chain (eMyHC), can also be used to gauge the extent of muscle regeneration, maintenance, or repair. For example, the presence of eMyHC can indicate that muscle regeneration has recently occurred in a subject.

Muscle cell regeneration, maintenance, or repair can also be monitored by determining the girth, or mean cross sectional area, of muscle cells or density of muscle fibers. Additional indicators of muscle condition include muscle weight and muscle protein content. Mitotic index (such as by measuring BrdU incorporation) and myogenesis can also be used to evaluate the extent of muscle regeneration.

In particular examples, the improvement in muscle condition, such as regeneration, compared with a control is at least about 10%, such as at least about 30%, or at least about 50% or more, including an at least 15%, at least 20%, at least 25%, at least 30%, at least 40%, at least 45%, at least 50%, at least 60%, at least 70%, at least 80%, at least 90%, including a 10% to 90% decrease, 20% to 80% increase, 30% to 70% increase or a 40% to 60% increase (e.g., a 10%, 20%, 30%, 40%, 50%, 60%, 70%, 80%, 90%, 95%, 100%, 200% or more increase).

Combination Treatment Methods

The disclosed methods for inhibiting or treating muscular dystrophy can be used alone or can be accompanied by administration of other anti-muscular dystrophy agents or therapeutic treatments. Any suitable anti-muscular dystrophy agent can be administered to a patient as part of a treatment regimen that includes inhibiting or treating muscular dystrophy. In particular examples, prior to, during, or following administration of an effective amount of an agent that reduces or inhibits one or more signs or symptoms associated with muscular dystrophy, the subject can receive one or more other therapies. In one example, the subject receives one or more treatments prior to administration of a disclosed miRNA modulatory agent. Examples of such therapies include, but are not limited to, laminin-111 protein therapy, which works to stabilize the sarcolemma and reduce muscle degeneration. In some examples, a source of muscle cells can be added to aid in muscle regeneration and repair. In some aspects of the present disclosure, satellite cells are administered to a subject in combination with laminin therapy. U.S. Patent Publication 2006/0014287, incorporated by reference herein to the extent not inconsistent with the present disclosure, provides methods of enriching a collection of cells in myogenic cells and administering those cells to a subject. In further aspects, stem cells, such as adipose-derived stem cells, are administered to the subject. Suitable methods of preparing and administering adipose-derived stem cells are disclosed in U.S. Patent Publication 2007/0025972, incorporated by reference herein to the extent not inconsistent with the present disclosure. Additional cellular materials, such as fibroblasts, can also be administered, in some examples.

Additional therapeutic agents include agents which enhance the effect of the disclosed methods, such as a component of the extracellular matrix, such as an integrin, dystrophin, dystroglycan, utrophin, or a growth factor. In some examples, the additional therapeutic agent reduces or enhances expression of a substance that enhances the formation or maintenance of the extracellular matrix. In some examples, the additional substance can include aggrecan, angiostatin, cadherins, collagens (including collagen I, collagen III, or collagen IV), decorin, elastin, enactin, endostatin, fibrin, fibronectin, osteopontin, tenascin, thrombospondin, vitronectin, and combinations thereof. Biglycans, glycosaminoglycans (such as heparin), glycoproteins (such as dystroglycan), proteoglycans (such as heparan sulfate), and combinations thereof can also be administered.

In some examples, growth stimulants such as cytokines, polypeptides, and growth factors such as brain-derived neurotrophic factor (BDNF), CNF (ciliary neurotrophic factor), EGF (epidermal growth factor), FGF (fibroblast growth factor), glial growth factor (GGF), glial maturation factor (GMF) glial-derived neurotrophic factor (GDNF), hepatocyte growth factor (HGF), insulin, insulin-like growth factors, kerotinocyte growth factor (KGF), nerve growth factor (NGF), neurotropin-3 and -4, PDGF (platelet-derived growth factor), vascular endothelial growth factor (VEGF), and combinations thereof may be administered with one of the disclosed methods.

When used in combination with the administration of one of the disclosed therapeutic agents targeting one or more of miRNAs associated with muscular dystrophy, the additional treatment methods described above can be administered or performed prior to, at the same time, or following the disclosed anti-muscular dystrophy therapy as appropriate for the particular patient, the additional symptoms associated with muscular dystrophy and the specific combination of therapies.

Samples

MicroRNA and/or vesicles can be isolated from a biological sample obtained from the subject. The biological sample obtained from the subject may be any appropriate sample. In some examples, a microRNA, vesicle or other biomarker is detected in a serum or plasma sample. The biological sample may also be a tissue sample or biopsy, from which microRNA and/or vesicles can be obtained. For example, if the sample is a solid sample, cells from the sample can be cultured and vesicle product induced.

The biological sample may be obtained through a third party, such as a party not performing the analysis of the microRNA. For example, the sample may be obtained through a clinician, physician, or other health care manager of a subject from which the sample is derived. In some embodiments, the biological sample is obtained by the same party analyzing the microRNA.

The volume of the biological sample used for analyzing microRNA can be in the range of between 0.1-20 mL, such as less than about 20, 15, 10, 9, 8, 7, 6, 5, 4, 3, 2, 1 or 0.1 mL. In some embodiments, the sample is about 0.1, 0.2, 0.3, 0.4, 0.5, 0.6, 0.7, 0.8, 0.9, 1.0, 1.5, 2, 3, 4, 5, 6, 7, 8, 9, 10, 11, 12, 13, 14, 15, 16, 17, 18, 19, or 20 mL. In some embodiments, the sample is about 1,000, 900, 800, 700, 600, 500, 400, 300, 250, 200, 150, 100, 75, 50, 25 or 10 µl. For example, a small volume sample could be obtained by a prick or swab.

In some embodiments, analysis of one or more microRNA in a biological sample is used to determine whether an additional biological sample should be obtained for analysis. For example, analysis of one or more microRNA in a serum sample can be used to determine whether a biopsy should be obtained. Similarly, analysis of one or more microRNA in a plasma sample can be used to determine whether a biopsy should be obtained.

The following example is provided to illustrate certain particular features and/or embodiments. This example should not be construed to limit the invention to the particular features or embodiments described.

Example

α7 integrin, β1 integrin and laminin-α2 transcripts have microRNA binding sites for miR-29 and miR124a that may coordinately regulate transcript levels. The inventors have shown expression of these miRNA's are altered in the skeletal muscle of mdx mice. In this example, the role microRNAs play in coordinating expression of α7 integrin, β1 integrin and laminin-α2 transcripts in normal and diseased muscle will be determined. Targeting these processes identify therapeutic targets for the treatment of muscular dystrophy, such as DMD.

Figure 1A:
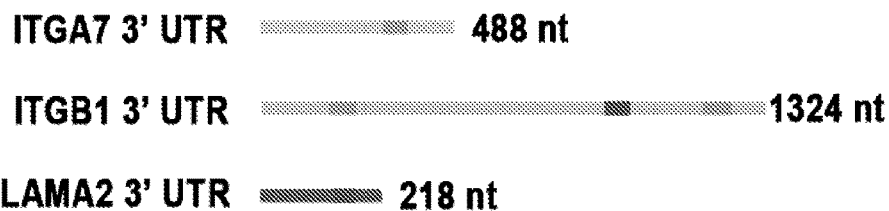
Figure 1A:
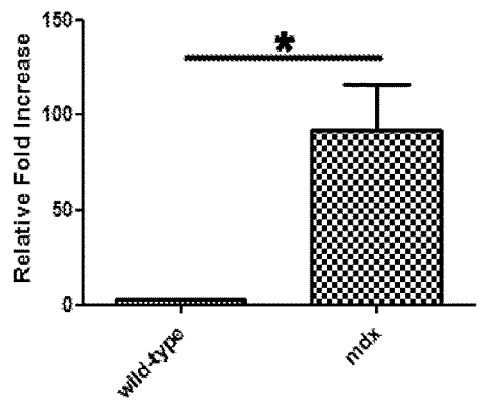
Figure 1A:
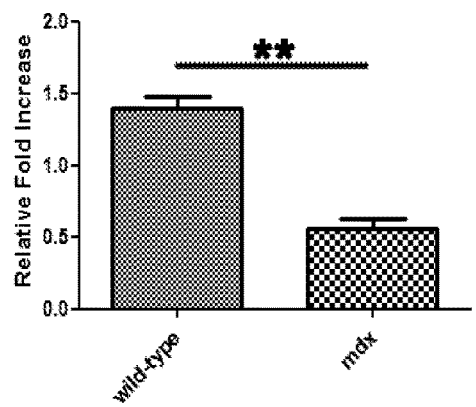
Figure 1D:
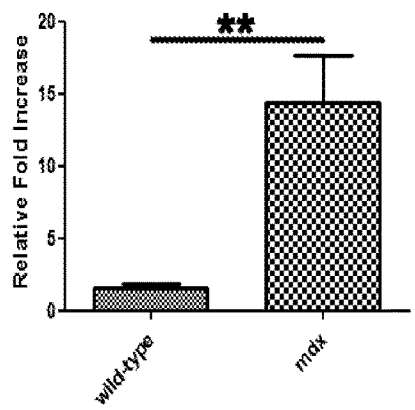
Figure 1E:
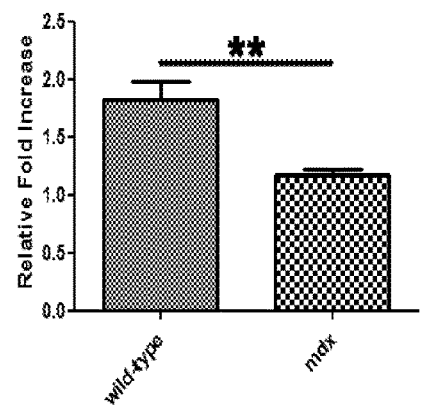

MicroRNAs (miRNAs) are small highly conserved non-coding RNAs that regulate mRNA stability, translation and can coordinate the expression of multiple genes including integrins. Initially, a bioinformatics search using TargetScan software for conserved miRNA binding sites within the 3' UTRs of ITGA7, ITGB1, and LAMA2 predicted a miRNA-124 site on ITGA7 and two on ITGB1 (FIG. 1A). Sites for miRNA-29 were also predicted on the ITGB1 and Lama2 transcripts (FIG. 1A) indicating that the entire complex might be regulated in a coordinated manner by two miRNAs. The inventors hypothesized that alteration of the levels of these miRNAs might be responsible for the increase in α7 Integrin transcript/protein levels observed in mdx mouse muscle compared to wild-type. In order to determine if miRNA-124 or miRNA-29 were altered in dystrophic muscle total RNA was isolated from either 3-month (n=3 each) or 12-month-old (n=5 each) wild-type and mdx mouse triceps with Trizol (Invitrogen) using standard procedures. The total RNA was then DNase treated, followed by qRT-PCR using Taqman primers for miRNA-124a or miRNA-29 in both mouse and human. Primers against U6 were used as normalization controls. The inventors found a significant increase in miRNA-124 levels in mdx mice at both 3-months (FIG. 1B, ~90-fold) and 12-months (FIG. 1D, ~8-fold) relative to wild-type levels. To the inventors' surprise, a significant downregulation of miRNA-29 levels were found in mdx mice at both 3-months (FIG. 1C, ~3-fold) and 12-months (FIG. 1E, ~2-fold) relative to wild-type levels. Together, this data indicates that miRNA-124 likely functions in a transcript stabilizing manner, whereas miRNA-29 likely functions in a more classical transcript destabilizing fashion.

Figure 1F:
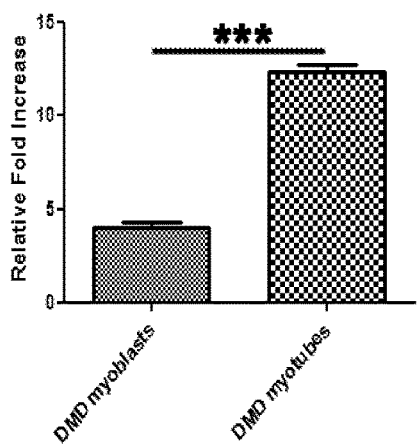
Figure 1G:
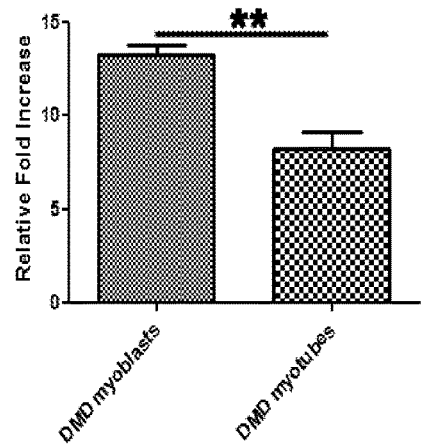

To determine whether miRNA-124a and miRNA-29 are the molecular mechanism responsible for the increased α7 integrin during myogenic differentiation, total RNA was isolated and purified from human DMD myoblasts before and after differentiation and examined miRNA-124a and miRNA-29 levels by qRT-PCR as described above. Human DMD myotubes displayed a 3-fold increase in miRNA-124a levels (FIG. 1F) and ~2-fold decrease in miRNA-29 levels (FIG. 1G) relative to myoblast levels. Therefore, the alteration of these miRNAs may be a normal part of the differentiative process to coordinate α7β1 integrin and laminin expression.

These results indicate miR-29 and miR-124a post-transcriptionally regulate α7β1 integrin and laminin-α2 in skeletal muscle. It is believed that miR-124a stabilizes α7β1 and laminin-a2 transcripts while miR-29 destabilizes these transcripts. miRNA binding to the 3'UTR of each target gene was verified using luciferase reporter assays. The 3'-UTR's of mouse ITGA7, ITGB1 and LAMA2 have been cloned into the dual psiCHECK promoter-Luciferase-Renilla vector system. In this system the Renilla transcript is regulated by the 3'-UTR of ITGA7, ITGB1 or LAMA2 genes. The constructs were transfected into HEK 293 cells expressing pmiR-124-1 or miR-29a and miR-29 and miR-124a regulation for each gene analyzed by measuring levels of Renilla luminescence in the cells using the Dual-Luciferase Assay detection system (Promega, Wis.) in a microtiter plate format. In addition, transfected test constructs and vector only C2C12 in both myoblasts and myotubes will be treated with PBS or 100 nM laminin-111 protein. To control for transfection efficiency, Renilla luminescence was normalized to firefly luciferase luminescence expressed from within the psiCHECK vector. Normalized luciferase activity was reduced upon transfection of wild-type ITGA7 or ITGB1 in HEK 293 cells expression pmiR-124-1 compared to cells expressing the control pmiR-H1 vector (FIG. 2B). This demonstrates that miR-124-1 binds the 3'UTR of these genes. Targeting of each miRNA to the corresponding 3'UTR was further confirmed by site-directed mutagenesis of the predicted miRNA-binding site. Mutations were introduced using Quikchange Lightning technology (Agilent) and primers by addition of a NdeI restriction site into the core miRNA-124 seed sequence, as shown in FIG. 2A. The mutant constructs were transfected in HEK 293 cells luminescence measured as above in comparison to the wild-type constructs. Mutation of the predicted 3'UTR ITGA7 seed sequence binding site significantly increased luciferase activity in cells transfected with the mutant construct compared to the wild-type in cells expression pmiR-124-1 (FIG. 2B). Mutations were also generated in both of the predicted 3'UTR ITGB1 binding sites and found increased luciferase activity compared the wild-type 3'UTR (FIG. 2C). FIG. 3 illustrates specific small molecules increase α7 Integrin levels also decrease miR-124 and miR-29 levels. In Human DMD myotubes, the levels of miR-124 and miR-29 were downregulated by MLS-969 treatment (a α7 integrin enhancing compound). A corresponding increase in ITGA7, ITGB1, and LAMA2 transcripts was observed with MLS-969 treatment. The compound structure for MLS-969 is

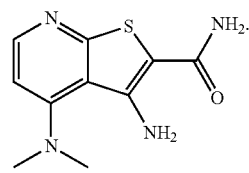 [SMILES: CN(C)c1ccnc2sc(C(N)=O)c(N)c12]

Further, FIG. 4 illustrates known inhibitors of integrin α7 Integrin expression regulate miR-124a expression Wild-type Smooth Muscle cells (WT SMC). WT SMC were plated at a density of 35,000 cells/6 well and grown in M199+FBS and growth factors prior to differentiation for 5 days in serum-free DMEM/F12. Cultures were then treated with 10 mM MG-132 for 48 hours. Total RNA was isolated to measure miRNA or mRNA.

Additional miRNA mimetics and inhibitors specific to miR-29a and miR-124a will be used to further investigate regulation of Itga7, Itgb1 and Lama2 transcript and protein in C2C12 and human DMD myoblasts and myotubes.

Double stranded miR-29a and miR-124a miRNAs mimetic chemically modified for strand selection and stability will be obtained from Ambion, along with a miRNA mimetic with a random non-binding nucleotide sequence to use as a negative control. Single stranded miRNA inhibitors designed to specifically bind to endogenous miRNA will also be purchased from Ambion. For in vitro studies, C2C12 myoblasts and myotubes will be treated with 0, 0.2, 2, 20 and 2000 nM of the miRNA mimetic or inhibitor for 48 hours based on published reports (Stenvang, J., A. Petri, M. Lindow, S. Obad, and S. Kauppinen. 2012. Inhibition of microRNA function by antimiR oligonucleotides. *Silence*. 3:1; Suzuki, H. I., K. Yamagata, K. Sugimoto, T. Iwamoto, S. Kato, and K. Miyazono. 2009. Modulation of microRNA processing by p 53. *Nature*. 460:529-533, each of which is hereby incorporated by reference in its entirety). Cells will be harvested for both RNA and protein. QRT-PCR will be performed assess the expression of miR-29a or miR124a in the presence of mimics or inhibitors and to quantify the transcript levels of ITGA7, ITGB1 and LAMA2 in the cells. Western analysis will be performed to detect alpha7 integrin, beta1 integrin and laminin-α2 protein in the cells. For both transcript and protein studies a dose response curve established for each treatment and $EC_{50}$ for miRNA mimetics and inhibitors determined.

Finally, α7 integrin enhancing compounds will be used to identify the molecular pathways that regulate α7 integrin expression in skeletal muscle. It will first be determined if these compounds regulate miR-29 and miR-124a levels in C2C12 and DMD myogenic cells. C2C12 and DMD myogenic cells will be grown as described above and differentiated into myotubes. IEC-9, 10, 11, 12, 13 or DMSO will be added to myotubes using the known $EC_{100}$ dose for each lead compound for 48 hours. All studies will be done in triplicate and RNA extracted using TriZol reagent (Invitrogen). RNA will be reverse transcribed to cDNA using a Superscript II kit (Invitrogen). Primer sequences will be to specifically amplify mouse or human miR-29 and miR-124a using TaqMan technology (Applied Biosystems Inc., Foster City, Calif.), and reactions carried out in an ABI Prism 7000 Sequence Detection System will be used. The CT value and a standard curve from a dilution series of cDNA from non-treated cells will be calculated by the accompanying ABI Prism 7000 SDS software. α7 integrin transcript will be normalized to U6 transcript and reported as fold change from control cells. Studies will be performed in triplicate wells of a 96-well plate. Statistical significance ($p<0.05$) will be determined using ANOVA.

PreMIR-29 and preMIR-124a will be used in vivo to examine if these can regulate Itga7, Itgb1 and Lama2 transcript and protein in the mdx mouse model of DMD and if they are therapeutic in the treatment muscular dystrophy. Doses of miR-29a and miR-124a mimetics used for in vivo studies will be determined from the in vitro studies described above. For each treatment group, 10 male mdx mice at 14 days of age will be injected daily by i.v. with preMIR control, preMIR-29 or preMIR-124. Sample size was determined by Power analysis with the expectation of a large effect in the treatment group (Power=0.8, a=0.05 and r=0.7). Animal weights will be recorded weekly. At 5 and 8 weeks of age, mice will be injected IP with 50 μl of sterile Evan's blue dye (EBD (10 μg/ml) per 10 g of body weight. EBD binds to albumin and is taken up by muscle cells with compromised membrane integrity. Mice will be sacrificed 24 hours after EBD injection and the Tibialis anterior (TA), gastrocnemius and diaphragm muscles harvested.

QRT-PCR will be used to quantify levels of miR-29 and miR-124a in muscle and transcript levels of Itga7, Itgb1 and Lama2 as outlined above in TA, gastrocnemius and diaphragm muscles. Protein levels of α7β1 integrin and laminin-α2 in TA, gastrocnemius and diaphragm muscles will be analyzed by semi-quantitative western blots analysis and by immunofluorescence. Tissue will be sectioned at 10 μm on a Leica CM1850 cryostat. Slides will be fixed using 4% paraformaldehyde and Evans blue dye uptake will be determined by outlining fibers with 2 μg/ml Oregon Green-488 wheat germ agglutinin. EBD positive myofibers will be counted at 400× magnification with those recording the data blinded to the test groups. The percentage of EBD positive myofibers in the TA and gastrocnemius muscles will be determined by counting at least 1000 muscle fibers per treatment group. Evans blue dye uptake will also be measured using lysate extracted from whole muscle as previously described (Heydemann, A., J. M. Huber, A. Demonbreun, M. Hadhazy, and E. M. McNally. 2005. Genetic background influences muscular dystrophy. *Neuromuscul. Disord.* 15:601-609). The data from each assay will be averaged and analyzed by ANOVA with a p-value<0.05 considered statistically significant.

DMD patient's exhibit elevated serum creatine kinase levels as a result of damaged muscle fibers. Serum creatine kinase will be measured using blood samples collected from retro-orbital bleeds from 10 male wild-type and mdx mice treated with preMIR control, preMIR-29 or preMIR-124. Blood from retro-orbital bleeds will be allowed to clot at room temperature for 30 minutes and serum will be separated by centrifuging samples at 3000 rpm for 10 minutes. Serum will be stored at −80° C. until analysis. Samples will be sent to the Comparative Pathology Laboratory at the University of California, Davis (Davis, Calif.) for analysis. Data will be analyzed by ANOVA and a P-value of <0.05 will be considered statistically significant.

To determine if preMIR-29 or preMIR-124a prevents exercise-induced muscle damage, 10 mdx mice at 10 days of age will be injected IV with preMIR control, preMIR-29 or preMIR-124. At 5 and 8 weeks of age mice will be placed on an Exer-3/6 treadmill (Columbus Instruments, Columbus, Ohio). A non-exercised group of 10 PBS-treated mdx mice will serve as a control to demonstrate the exercise protocol induced muscle damage. The speed of the treadmill will be gradually increased from 10 to 15 m/min during a 2 min warm-up period. Mice will be subjected to a single downhill running exercise protocol (−12°, 15 m/min, 25-30 min) as previously reported (Rooney, J. E., P. B. Gurpur, and D. J. Burkin. 2009a. Laminin-111 protein therapy prevents muscle disease in the mdx mouse model for Duchenne muscular dystrophy. *Proc. Natl. Acad. Sci. U.S.A.* 106:7991-7996). Mice will be injected with Evan's blue dye and TA, gastrocnemius, diaphragm and heart harvested 24 hours later. Tissues will be sectioned on a Leica CM1850 cryostat to 10 μm and sections fixed using 4% paraformaldehyde. Evans blue dye uptake will be determined as outlined above. Data will be analyzed by ANOVA and a p-value of <0.05 will be considered statistically significant. To examine if IEC-10 improves the mechanical and contractile properties of dystrophin deficient muscle, 10 male wild-type and mdx mice treated with preMIR control, preMIR-29 or preMIR-124. The mechanical and contractile properties and fatiguability of EDL, soleus and diaphragm muscle strips will be assessed using procedures described herein. Data will be analyzed by ANOVA and a p-value of <0.05 will be considered statistically significant.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, comprising:
   administering to a subject with Duchenne muscular dystrophy (DMD) an effective amount of an antisense compound that downregulates miRNA-124 expression, thereby down-regulating miRNA-124 expression in the subject with DMD.

2. The method of claim 1, wherein the antisense compound is an antisense oligonucleotide, siRNA or ribozyme.

3. The method of claim 1, wherein the antisense compound downregulates miRNA-124 by decreasing expression of miRNA-124-1, miRNA-124-2, miRNA-124-3, or a combination thereof.

4. The method of claim 1, further comprising administering MLS-969.

5. The method of claim 4, wherein the antisense compound that downregulates miRNA-124 and MLS-969 are administered simultaneously.

6. The method of claim 4, wherein the antisense compound that downregulates miRNA-124 is administered prior to administration of MLS-969.

7. The method of claim 1, wherein the subject is a human.

8. The method of claim 1, further comprising diagnosing a subject with DMD by:
   detecting expression of at least one microRNA (miR) gene product in a sample obtained from the subject, wherein the at least one miR gene product comprises at least miRNA-124; and
   comparing expression of at least one of the miR gene product in the sample obtained from the subject to a control,
   wherein altered expression of the at least one miR gene product in the sample obtained from the subject, including at least increased expression in miRNA-124, compared to the control identifies a subject with DMD.

9. The method of claim 8, wherein the at least one miR gene product comprises miRNA-124 and miRNA-29.

10. The method of claim 8, wherein altered expression comprises an at least two-fold increase in miRNA-124.

11. The method of claim 9, wherein altered expression comprises an at least two-fold increase in miRNA-124 and an at least two-fold decrease in miRNA-29.

12. The method of claim 8, wherein the antisense compound downregulates miRNA-124 by decreasing expression of miRNA-124-1, miRNA-124-2, miRNA-124-3, or a combination thereof.

13. The method of claim 8, further comprising administering MLS-969.

* * * * *